(12) United States Patent
Shi et al.

(10) Patent No.: US 10,098,913 B2
(45) Date of Patent: Oct. 16, 2018

(54) COMPOSITION OF STEM CELLS HAVING HIGHLY EXPRESSED FAS LIGAND

(71) Applicant: UNIVERSITY OF SOUTHERN CALIFORNIA, Los Angeles, CA (US)

(72) Inventors: Songtao Shi, Thousand Oaks, CA (US); Shiyu Liu, Los Angeles, CA (US); Fa-ming Chen, Xian (CN)

(73) Assignee: University Of Southern California, Los Angeles, CA (US)

( * ) Notice: Subject to any disclaimer, the term of this patent is extended or adjusted under 35 U.S.C. 154(b) by 0 days.

(21) Appl. No.: 14/915,105

(22) PCT Filed: Sep. 10, 2014

(86) PCT No.: PCT/US2014/055024
§ 371 (c)(1),
(2) Date: Feb. 26, 2016

(87) PCT Pub. No.: WO2015/038665
PCT Pub. Date: Mar. 19, 2015

(65) Prior Publication Data
US 2016/0206660 A1 Jul. 21, 2016

Related U.S. Application Data

(63) Continuation-in-part of application No. PCT/US2014/043918, filed on Jun. 24, 2014.

(60) Provisional application No. 61/876,694, filed on Sep. 11, 2013.

(51) Int. Cl.
*A61K 35/28* (2015.01)
*C12N 5/0775* (2010.01)

(52) U.S. Cl.
CPC ............ *A61K 35/28* (2013.01); *C12N 5/0662* (2013.01); *C12N 5/0663* (2013.01); *C12N 5/0668* (2013.01); *C12N 2501/25* (2013.01); *C12N 2501/999* (2013.01); *C12N 2502/30* (2013.01)

(58) Field of Classification Search
None
See application file for complete search history.

(56) References Cited

U.S. PATENT DOCUMENTS

| 5,900,412 A | 5/1999 | Traue et al. |
| 2004/0131599 A1 | 7/2004 | Civin et al. |
| 2008/0051332 A1 | 2/2008 | Templin |
| 2011/0206645 A1 | 8/2011 | Zhang et al. |
| 2012/0177736 A1 | 7/2012 | Plachetka |

FOREIGN PATENT DOCUMENTS

| WO | 2012/012570 A2 | 1/2012 |
| WO | WO2012009581 A2 | 1/2012 |
| WO | WO2013149211 A2 | 10/2013 |

OTHER PUBLICATIONS

Lu et al., Can. Biol. Ther., 7(2):245-251 (2008).*
Akiyama et al., Cell Stem Cell (10(5):544-555 (2012).*
Zhang et al., J. Immunol., 183(12):7787-7798 (2009).*
Pant et al., Biol. Blood Marrow Transplant., 13:877-885 (2007).*
Bjorkstrand et al., Blood, 88(12):4711-4718 (1996).*
Drobyski et al., Bone Marrow Transplant., 43:169-177 (2009).*
Murphy et al., Cell Stem Cell, 10: 485-486 (2012).*
Xu et al., Stem Cells, 30:266-279 (2012).*
Zhang et al., Leuk. Lymph., 4693):425-433 (2005).*
Atsuta, I. et al. 2013. Mesenchymal stem cells inhibit multiple myeloma cells via the Fas/Fas ligand pathway. Stem Cell Research & Therapy 2013, vol. 4, pp. 111-124.
Chen, C. et al. 2014. Telomerase governs immunomodulatory properties of mesenchymal stem cells by regulating FAS ligand expression. EMBO Molecular Medicine, vol. 6, No. 3, pp. 322-334.
ISA/USPTO. 2014. International Search Report & Written Opinion of the International Searching Authority, dated Dec. 19, 2014, for PCT Application PCT/US2014/055024, filed Sep. 10, 2014 (PCT parent of instant national phase application).
Yamaza et al., "Pharmacologic Stem Cell Based Intervention as a New Approach to Ost4eoporosis Treatment in Rodents," PLOS ONE, vol. 3, No. 7, Jul. 2008.
Li et al., "Therapeutic effects of intrabone and systemic mesenchymal stem cell cytotherapy on myeloma bone disease and tumor growth," Journal of Bone and Mineral Research, vol. 27, No. 8, Aug. 2012, pp. 1635-1648.
Tang et al., Aspirin Treatment Improved Mesenchymal Stem Cell Immunomodulatory Properties via the 15d-PGJ2/PPARγ/TGF-β1 Pathway.
Extended European Search Report from European Patent Application No. 14843715.5, dated Apr. 21, 2017.
Keramidas M, de Fraipont F, Karageorgis A, Moisan A, Persoons V, Richard M J, Coll J L, Rome C: The dual effect of mesenchymal stem cells on tumour growth and tumour angiogenesis. Stem Cell Res Ther 2013, 4:41.
Prather WR, Toren A, Meiron M: Placental-derived and expanded mesenchymal stromal cells (PLX-I) to enhance the engraftment of hematopoietic stem cells derived from umbilical cord blood. Expert Opin Biol Ther 2008, 8:1241-1250.

(Continued)

Primary Examiner — Thomas J. Visone
(74) Attorney, Agent, or Firm — McDermott Will & Emery LLP

(57) ABSTRACT

This disclosure relates in general to a stem cell treatment. This disclosure further relates to a stem cell treatment using a composition comprising stem cells having highly expressed Fas-L. This disclosure further relates to a stem cell treatment of multiple myeloma. This disclosure also relates to a composition comprising stem cells having highly expressed Fas-L. This disclosure also relates to preparation of a composition comprising stem cell having highly expressed Fas-L. This disclosure also relates to preparation of a composition comprising stem cells having highly expressed Fas-L by using a salicylate. An example of salicylate may be aspirin. This disclosure further relates to a stem cell treatment of multiple myeloma. This disclosure also relates to a stem cell treatment of an inflammatory disease and/or autoimmune disease.

13 Claims, 20 Drawing Sheets

(56) References Cited

OTHER PUBLICATIONS

Zappia E, Casazza S, Pedemonte E, Benvenuto F, Bonanni I, Gerdoni E, Giunti D, Ceravolo A, Cazzanti F, Frassoni F, Mancardi G, Uccelli A: Mesenchymal stem cells ameliorate experimental autoimmune encephalomyelitis inducing T cell anergy. Blood 2005, 106:1755-1761.

ParekkadanB, TillesA W, YarmushM L: Bone marrow-derived mesenchymal stem cells ameliorate autoimmune enteropathy independently ofregulatory T cells. Stem Cells 2008, 26:1913-1919.

Prockop DJ: Repair of tissues by adult stem/ progenitor cells (MSCs ): controversies, myths, and changing paradigms. Mo! Ther 2009, 17:939-946.

Uccelli A, Moretta L, Pistoia V: Mesenchymal stem cells in health and disease. Nat Rev Immunol 2008, 8:726-736.

Xu B, Xu Z, Xia T, He P, Gao P, He W, Zhang M, Guo L, Niu Q, Wang A: Effects of the Fas/Fas-L pathway on fluoride-induced apoptosis in SH-SY5Y cells. Environ Toxicol 2011, 26:86-92.

Garcia-Santos G, Martin V, Rodriguez-Blanco J, Herrera F, Casado-Zapico S, Sanchez-Sanchez AM, Antolin I, Rodriguez C: Fas/Fas ligand regulation mediates cell death in human Ewing's sarcoma cells treated with melatonin. Br J Cancer 2012, 106:1288-1296.

O'Connell J, Houston A, Bennett M W, O'Sullivan G C, Shanahan F: Immune privilege or inflammation? Insights into the Fas ligand enigma. Nat Med 2012, 7:271-274. 2001.

Yang X, Yang C, Shao K, Ye X, Meng H, Zhou Y, Qian W: Refractory multiple myeloma treated with homoharringtonine: report of two cases Ann Hematol 2007, 86:919-921.

Lou Y J, Qian W B, Jin J: Homoharringtonine induces apoptosis and growth arrest in human myeloma cells. Leuk Lymphoma 2007, 48:1400-1406.

Khakoo A Y, Pati S, Anderson SA, Reid W, Elshal MF, Rovira I I, Nguyen AT, Mali de D, Combs CA, Hall G, Zhang J, Raffeld M, Rogers TB, Stetler-Stevenson W, Frank J A, Reitz M, Finkel T: Human mesenchymal stem cells exert potent antitumorigenic effects in a model of Kaposi's sarcoma. J Exp Med 2006, 203:1235-1247.

Bergsagel PL, Kuehl WM: Molecular pathogenesis and a consequent classification of multiple myeloma. J Clin Oneal 2005, 23:6333-6338.

Yaccoby S: Advances in the understanding of myeloma bone disease and tumour growth. Br J Haematol 2010, 149:311-321.

Giuliani N, Rizzoli V, Roodman GD: Multiple myeloma bone disease: pathophysiology of osteoblast inhibition. Blood 2006, 108:3992-39996.

Walker R, Barlogie B, Haessler J, Tricot G, Anaissie E, Shaughnessy J D Jr, Epstein J, van Hemert R, Erdem E, Haering A, Crowley J, Ferris E, Hollmig K, van Rhee F, Zangari M, Pineda-Roman M, Mohiuddin A, Yaccoby S, Sawyer J, Angtuaco E J: Magnetic resonance imaging in multiple myeloma: diagnostic and clinical implications. J Clin Oncol 2007, 25:1121-1128.

Li X, Ling W, Khan S, Yaccoby S: Therapeutic effects of intrabone and systemic mesenchymal stem cell cytotherapy on myeloma bone disease and tumor growth. J Bone Miner Res 2012, 27:1635-1648.

Jemal A, Graubard BI, Devesa S S, Flegal KM:The association of blood lead level and cancer mortality among whites in the United States. Environ Health Perspect 2002, 110:325-329.

Giuliani N, Colla S, Morandi F, Lazzaretti M, Sala R, Bonomini S, Grano M, Colucci S, Svaldi M, RizzoliV: Myeloma cells block RUNX2/CBFA1 activity in human bone marrow osteoblast progenitors and inhibit osteoblast formation and differentiation. Blood 2005, 106:2472-2483.

Li X, Pennisi A, Yaccoby S: Role of decorin in the antimyeloma effects of osteoblasts. Blood 2008, 112: 159-168 [0027].

Giuliani N, Mangoni M, Rizzoli V: Osteogenic differentiation of mesenchymal stem cells in multiple myeloma: identification of potential therapeutic targets. Exp Hematol 2009, 37:879-886.

Yaccoby S, Ling W, ZhanF, WalkerR, Barlogie B, Shaughnessy JD Jr: Antibody-based inhibition ofDKKI suppresses tumor-induced bone resorption and multiple myeloma growth in vivo. Blood 2007, 109:2106-2111.

Vallet S, Pozzi S, Patel K, Vaghela N, Fulciniti MT, Veiby P, Hideshima T, Santo L, Cirstea D, Scadden D T, Anderson KC, Raje N: A novel role for CCL3 (MIP-lalpha) in myeloma-induced bone disease via osteocalcin downregulation and inhibition of osteoblast function. Leukemia 2011, 25:1174-1181.

Gasparetto C: Stem cell transplantation for multiple myeloma. Cancer Control 2004, 11: 119-129.

Suzuki K, Sun R, Origuchi M, Kanehira M, Takahata T, ItohJ, Umezawa A, Kijima H, Fukuda S, Saijo Y: Mesenchymal stromal cells promote tumor growth through the enhancement of neovascularization. Mo! Med 2011, 17:579-587.

Klopp AH, Gupta A, Spaeth E, Andreeff M, Marini F 3rd: Concise review: Dissecting a discrepancy in the literature: do mesenchymal stem cells support or suppress tumor growth? Stem Cells 2011, 29:11-19.

Li X, Ling W, Pennisi A, Wang Y, Khan S, Heidaran M, Pal A, Zhang X, He S, Zeitlin A, Abbot S, Faleck H, Hariri R, Shaughnessy JD Jr, van Rhee F, Nair B, Barlogie B, Epstein J, Yaccoby S: Human placenta-derived adherent cells prevent bone loss, stimulate bone formation, and suppress growth of multiple myeloma in bone. Stem Cells 2011, 29:263-273.

Chen L, Wang S, Zhou Y, Wu X, Entin I, Epstein J, Yaccoby S, Xiong W, Barlogie B, Shaughnessy JD Jr, Zhan F: Identification of early growth response protein 1 (EGR-1) as a novel target for JUN-induced apoptosis in multiple myeloma. Blood2010, 115:61-70.

Waterman R S, Henkle S L, Betancourt A M: Mesenchymal stem cell 1 (MSCI)-based therapy attenuates tumor growth whereas MSC2-treatment promotes tumor growth and metastasis. PLoS One 2012, 7:e45590.

Gunn W G, Conley A, Deininger L, Olson SD, Prockop D J, Gregory C A: A crosstalk between myeloma cells and marrow stromal cells stimulates production of DKKI and interleukin-6: a potential role in the development of lytic bone disease and tumor progression in multiple myeloma. Stem Cells 2006, 24: 986-991.

Eter ME, Budd RC, Desbarats J, Hedrick S M, Hueber A 0, Newell MK, Owen LB, Pope RM, Tschopp J, Wajant H, Wallach D, Wiltrout RH, Ziimig M, Lynch DH: The CD95 receptor: apoptosis revisited. Cell 2007, 129:447-450.

Strasser A, Jost P J, Nagata S: The many roles of Fas receptor signalling in the immune system. Immunity 2009, 30:180-192.

Suda T, Takahashi T, Golstein P, Nagata S: Molecular cloning and expression of the Fas ligand, a novel member of the tumor necrosis factor family. Cell 1993, 75:1169-1178.

Lettau M, Paulsen M, Kabelitz D, Janssen 0: Storage, expression and function of Fas ligand, the key death factorofimmune cells. Curr Med Chem 2008, 15: 1684-1696.

Mazar J, Thomas M, Bezrukov L, ChanturiaA, Pekkumaz G, Yin S, Kuznetsov SA, Robey PG, Zimmerberg J: Cytotoxicity mediated by the Fas ligand (FasL)-activated apoptotic pathway in stem cells. J Biol Chem 2009, 284: 22022-22028.

LeBlanc R, Catley LP, Hideshima T, Lentzsch S, Mitsiades C S, Mitsiades N, Neuberg D, Goloubeva 0, Pien C S, Adams J, Gupta D, Richardson P G, Munshi N C, Anderson KC: Proteasome inhibitor PS-341 inhibits human myeloma cell growth in vivo and prolongs survival in a murine model. Cancer Res 2002, 62:4996-5000.

Liu Y, Wang L, Kikuiri T, Akiyama K, Chen C, Xu X, Yang R, Chen W, Wang S, Shi S: Mesenchymal stem cell-based tissue regeneration is governed by recipient T lymphocytes via IFN-y and TNF-a. Nat Med 2011, 17:1594-1601.

Oyajobi B 0, Franchin G, Williams P J, Pulkrabek D, Gupta A, Munoz S, Grubbs B, Zhao M, Chen D, Sherry B, Mundy G R: Dual effects of macrophage inflammatory protein-I alpha on osteolysis and tumor burden in the murine 5TGM1 model of myeloma bone disease. Blood 2003, 102:311-319.

Akiyama K, Chen C, Wang D, Xu X, Qu C, Yamaza T, Cai T, Chen W, SunL, Shi S: Mesenchymal-stemcell-induced immunoregulation involves FAS-ligand-/FASmediated T cell apoptosis. Cell Stem Cell 2012, 10:544-555.

Musto P, D'Auria F: Melphalan: old and new uses of a still master drug for multiple myeloma. Expert Opin Investig Drugs 2007, 16:1467-1487.

(56) References Cited

OTHER PUBLICATIONS

Zhang Q, Shi S, Liu Y, Dyanne J, Shi Y, Shi S, Le AD: Mesenchymal stem cells derived from human gingiva are capable of immunomodulatory functions and ameliorate inflammation-related tissue destruction inexperimental colitis. J Immunol 2009, 183:7787-7798.

SunL Y, ZhouKX, FengXB, Zhang HY, Ding X Q, Jin 0, Lu L W, Lau CS, Hou YY, Fan L M: Abnormal surface markers expression on bone marrow CD34+ cells and correlation with disease activity in patients with systemic lupus erythematosus. Clin Rheumatol 2007, 26:2073-2079.

Dorner T, Lipsky PE: Signalling pathways in Bcells: implications for autoimmunity. Curr Top Microbial Immunol 2006, 305:213-240.

Vejlgaard T, Abildgaard N, Jans H, Nielsen J L, Heickendorff L: Abnormal bone turnover in monoclonal gammaopathy of undetermined significance: analyses of type I collagen telopeptide, osteocalcin, bone-specific alkaline phosphatase and propeptides of type I and type III procollagens. Eur J Haematol 1997, 58:104-108.

Hjorth-Hansen H, Seifert MF, Biirset M, Aarset H, Ostlie A, Sundan A, Waage A: Marked osteoblastopenia and reduced bone formation in a model of multiple myeloma bone disease in severe combined immunodeficiency mice. J Bone Miner Res 1999, 14:256-263.

Pennisi A, Ling W, Li X, Khan S, Shaughnessy J D Jr, Barlogie B, Yaccoby S: The ephrinB2/EphB4 axis is dysregulated in osteoprogenitors from myeloma patients and its activation affects myeloma bone disease and tumor growth. Blood 2009, 114: 1803-1812.

Oshima T, Abe M, Asano J, Hara T, Kitazoe K, Sekimoto E, Tanaka Y, Shibata H, Hashimoto T, Ozaki S, Ki do S, Inoue D, Matsumoto T: Myeloma cells suppress bone formation by secreting a soluble Wnt inhibitor, sFRP-2. Blood 2005, 106:3160-3165.

Bataille R, Manolagas S C, Berenson J R: Pathogenesis and management of bone lesions in multiple myeloma. Hematol Oneal Clin North Am 1997, 11:349-361.

Gregory CA, Gunn W G, Reyes E, Smalarz A J, Munoz J, Spees J L, Prockop D J: How Wnt signaling affects bone repair by mesenchymal stem cells from the bone marrow. Ann NY Acad Sci 2005, 1049:97-106.

Glass D A, Patel M S, Kassenty G: A new insight into the formation of osteolytic lesions in multiple myeloma. N Engl J Med 2003, 349:2479-2480.

Fu J, Wang P, Zhang X, Ju S, Li J, Li B, Yu S, Zhang J, Zhang X: Myeloma cells inhibit osteogenic differentiation of mesenchymal stem cells and kill osteo blasts via TRAIL-induced apoptosis. Arch Med Sci 2010, 6:496-504.

Mitsiades C S, McMillin D W, Klippel S, Hideshima T, Chauhan D, Richardson P G, Munshi N C, Anderson KC: The role of the bone marrow microenvironment in the pathophysiology of myeloma and its significance in the development of more effective therapies. Hematol Oneal Clin North Am 2007, 21:1007-1034. vii-viii.

Wang X, Zhang Z, Yao C: Survivin is upregulated in myeloma cell lines cocultured with mesenchymal stem cells. Leuk Res 2010, 34:1325-1329.

Coffelt S B, Marini F C, Watson K, Zwezdaryk K J, Dembinski J L, LaMarca H L, Tomchuck SL, Honer Z U, Bentrup K, Danka E S, Henkle S L, Scandurra A B: The pro-inflammatory peptide LL-37 promotes ovarian tumor progression through recruitment of multipotent mesenchymal stromal cells. Proc NatlAcad Sci USA 2009, 106:3806-3811.

Corre J, Labat E, Espagnolle N, Hebraud B, Avet-Loiseau H, Roussel M, Huynh A, Gadelorge M, Cordelier P, Klein B, Moreau P, Facon T, Fournie J J, Attal M, Bourin P: Bioactivity and prognostic significance of growth differentiation factor GDF15 secreted by bone marrow mesenchymal stem cells in multiple myeloma. Cancer Res 2012, 72: 1395-1406.

Shinagawa K, Kitadai Y, Tanaka M, Sumida T, Kodama M, Higashi Y, Tanaka S, Yasui W, Chayama K:Mesenchymal stem cells enhance growth and metastasis of colon cancer. Int J Cancer 2010, 127:2323-2333.

Albarenque S M, Zwacka R M, Mohr A: Both human and mouse mesenchymal stem cells promote breast cancer metastasis. Stem Cell Res 2011, 7: 163-171.

Ma Y, Hao X, Zhang S, Zhang J: The in vitro and in vivo effects of human umbilical cord mesenchymal stem cells on the growth ofbreast cancer cells. Breast Cancer Res Treat 2012, 133:473-485.

Caligaris-Cappia F, Bergui L, Gregoretti MG, Gaidano G, Gaboli M, Schena M, Zallone A Z, Marchisio P C: Role of bone marrow stromal cells in the growth of human multiple myeloma. Blood 1991, 77:2688-2693.

Ciavarella S, Grisendi G, Dominici M, Tucci M, Brunetti 0, Dammacco F, Silvestris F: In vitro anti-myeloma activity of TRAIL-expressing adipose-derived mesenchymal stem cells. Br J Haematol 2012, 157:586-598.

Chen FM, Zhao Y M, Jin Y, Shi S: Prospects for translational regenerative medicine. Biotechnol Adv 2012, 30:658-672.

Games C M: The dual role of mesenchymal stem cells in tumor progression. Stem Cell Res Ther 2013, 4:42.

\* cited by examiner

*FIG. 1G*
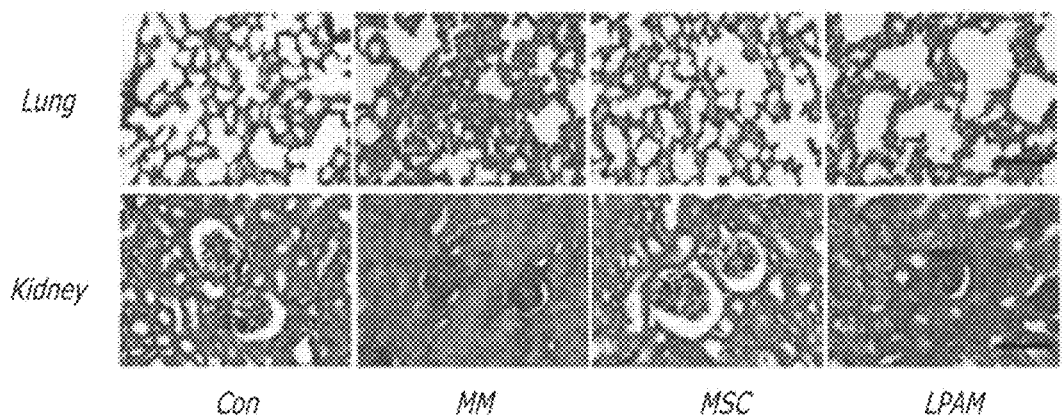
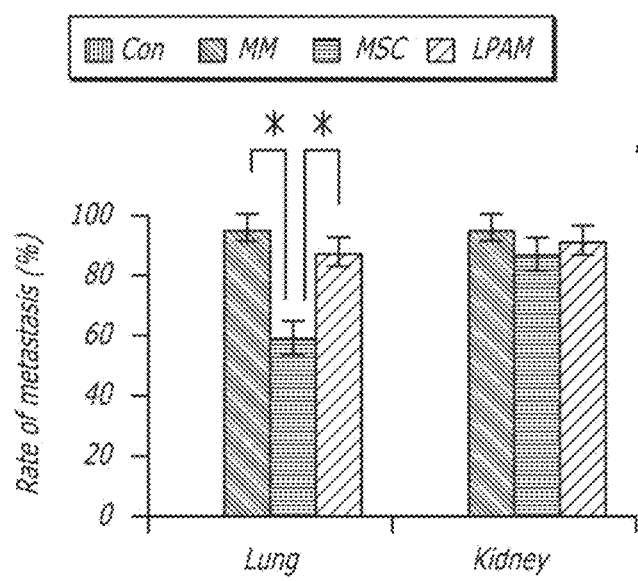
*FIG. 1H*

|  | Size of cancroid pearl | | | Gait disorder |
| --- | --- | --- | --- | --- |
|  | 5mm> | 10mm> | >10mm | |
| Con | 0 | 0 | 0 | 0 |
| MM | 0 | 10 | 4 | 5 |
| MSC | 9 | 3 | 2 | 2 |
| MSC(gld) | 0 | 5 | 9 | 8 |
| MSC(Asp) | 13 | 1 | 0 | 0 |

COMPOSITION OF STEM CELLS HAVING HIGHLY EXPRESSED FAS LIGAND

CROSS-REFERENCE TO RELATED APPLICATION

This application is a United States national phase application under 35 U.S.C. 371 of PCT Application PCT/US2014/055024, filed Sep. 10, 2014, entitled "A Composition of Stem Cells Having Highly Express FAS Ligad," attorney docket no. 064693-0361; which is based upon and claims priority to U.S. provisional patent application 61/876,694, entitled "Stem Cell Compositions and Methods for Inhibition of Multiple Myeloma Cells via the Fas-L/Fas Pathway," filed Sep. 11, 2013, attorney docket number 374634-000440. This application is also a continuation-in-part of Patent Cooperation Treaty (PCT) application number PCT/US2014/043918, "A Composition of Mesenchymal Stem Cells" filed Jun. 24, 2014, attorney docket number 094852-0019. The entire contents of each of these patent applications are incorporated herein by reference.

STATEMENT REGARDING FEDERALLY SPONSORED RESEARCH

This disclosure was made with Government support under Contract No. R01DE017449 awarded by the National Institutes of Health, Department of Health and Human Services. The Government has certain rights in the invention.

TECHNICAL FIELD

This disclosure relates in general to a stem cell treatment. This disclosure further relates to a stem cell treatment using a composition comprising stem cells having highly expressed Fas-L. This disclosure further relates to a stem cell treatment of multiple myeloma. This disclosure also relates to a composition comprising stem cells having highly expressed Fas-L. This disclosure also relates to preparation of a composition comprising stem cells having highly expressed Fas-L. This disclosure also relates to preparation of a composition comprising stem cells having highly expressed Fas-L by using aspirin.

DESCRIPTION OF RELATED ART

Multiple myeloma (MM) is the second most common hematological malignancy, with a yearly incidence of 14,000 in the United States, constituting 13% of blood cancers and 1% of all human cancers [1]. (The one digit or two digit numbers in the box brackets, i.e. [1] to [62], correspond to the numbers in the box brackets before each reference disclosed in the related art references section of this disclosure.) MM is unique among most hematological malignancies, with a high capacity to induce osteolytic bone lesions through the suppression of osteoblastogenesis, stimulation of osteoclastogenesis and the subsequent uncoupling of bone resorption and bone formation in areas adjacent to tumor foci in the bone marrow [2]. The occurrence of bone lesions is thus one of the major characteristics of MM patients [3]; the number of osteolytic or focal lesions has been associated with clinical disease progression for patients with MM [4]. More than 80% of MM patients suffer from large osteolytic lesions, and a lack of clinically effective therapeutics leads to the increasing severity of skeletal complications and, indeed, death as a result of lowered resistance to infection (that is, immunodeficiency), hypercalcemia, anemia, and renal failure, among others [5]. It is estimated that MM, with a median overall survival of 3 to 5 years, accounts for approximately 20% of deaths from hematologic malignancy and 1 to 2% of cancer-related deaths overall [6]. Currently, cure is a realistic goal for only a small minority of MM patients. The high morbidity and mortality rates associated with plasma cell malignancy have led to an increased demand for the effective management of this condition.

It is now generally accepted that MM bone disease is a reflection of osteoblast deactivation [3, 7]. The correction of osteoblast function in the bone of MM patients, therefore, has long been a primary target for the design of therapeutics for MM-related bone disease. To this end, bisphosphonates, such as pamidronate, and novel agents, such as lenalidomide, dasatinib, and bortezomib, which inhibit osteoclast activity and/or activate osteoblasts, have been identified for treatment of MM-induced osteoblast deactivation [2, 8]. Increased knowledge of the signaling pathways involved in the regulation of osteoblast formation and differentiation from MSCs might provide a better understanding of the pathophysiological mechanisms involved in MM-induced osteoblast inhibition and permit the development of more potential therapeutic agents against bone damage [2, 8, 9]. In this regard, novel osteoblast-activating agents, such as dickkopf-1-neutralizing antibody [10] and inhibitor of activin A signaling [11], are explored for the clinical treatment of MM bone disease. The combination of traditional cytotoxic and novel agents has led to higher response rates and improved long-term survival compared with treatment with standard doses of chemotherapy alone. Unfortunately, not all patients will respond to established novel agents, and even those who do respond will ultimately relapse or become refractory to currently available regimens. Moreover, large lytic lesions are typically not repaired, even after long term remission, and relapses often occur in pre-existing lesions [4]. Consequently, additional approaches are urgently needed to achieve systemic bone anabolism and repair large osteolytic lesions.

The use of mesenchymal stem cells (MSCs), also called mesenchymal stem cells, to treat MM bone disease has received considerable attention in the field of stem cell research [12]. However, whether MSC infusion inhibits or promotes cancer growth remains controversial. A number of in vitro studies suggest that MSCs from MM patients possess abnormal genomic, phenotypic, and functional properties, which might contribute to impaired bone formation in this disease by supporting and protecting MM cells from spontaneous and drug-induced apoptosis [9]. Furthermore, recent evidence shows that MSCs, when injected subcutaneously, promote tumor growth and neovascularization in syngeneic mouse models through directly supporting the tumor vasculature and secreting proangiogenic factors [13]. Indeed, the promotion of tumor growth through MSCs has also been observed in various cancer models (reviewed in [14]), suggesting that, at least in some specific conditions, MSCs play important roles in tumor progression.

In contrast with evidence supporting the fact that MSCs stimulate tumor growth, other studies have documented the routine suppression of tumor growth through MSCs (also reviewed in [14]). In particular, exogenously administered MSCs effectively promote bone formation and inhibit bone disease and the growth of highly aggressive MM cells in the bone, although the majority of systemically injected MSCs were localized in the lungs or in draining lymph nodes [15]. Furthermore, intrabone-injected MSCs have been demonstrated to act as bystander cells to promote bone formation, inhibit osteolysis, and delay MM growth and regrowth [5, 15]. New insights into the effects of in vivo milieu on MSC functions might explain these contradicting results [16, 17]. Notably, a high dose of melphalan with autologous stem cell support has played an integral part in MM therapy for more than 25 years, either as salvage therapy or to consolidate initial remission, although these therapeutic regimens typically utilize MM cells as adjuvants for other therapeutic agents [12]. Moreover, after MSC transplantation in over 1,000 patients with a clinically acceptable safety profile, not a single case of MSC-related tumors has been reported in a variety of indications [14]. Conceptually, it is a small leap from the adjuvant use of stem cells to novel cell-based therapies to enhance the therapeutic outcome of MM, but the idea has only recently begun to gain momentum.

The clinical and molecular characteristics of MM-related osteolytic lesions support the potential success of cell-based therapies for this disease [5, 12, 15], where the exogenous administration of healthy MSCs might affect MM bone disease via the secretion of trophic factors, instead of, or in addition to, directly participating in the regeneration of the damaged bone [12]. Gunn and colleagues showed that an interaction between MM cells and MSCs from the bone marrow stroma stimulated the production of dickkopf-1 and IL-6, resulting in the formation and persistence of osteolytic bone lesions [18]. These authors also showed that the Wnt signaling activator 6-bromoindirubin-3'-monoxime might release MSCs from the osteoinhibitory effects of Dickkopf-1, enabling released MSCs to repair existing osteolytic lesions [18]. Following the adjuvant use of stem cells for MM therapy [12], Li and colleagues proposed a proof-of-concept that healthy MSCs, independent of other therapeutic agents, might attenuate the growth of MM and suppress MM-induced bone disease through the inhibition of osteoclastogenesis and stimulation of endogenous osteoblastogenesis [5, 15]. Taken together, these data lead to new insights into, and the further exploration of, stem cell-based therapeutics for MM patients.

In addition to altering the bone marrow milieu that favors MM cell accommodation, the therapeutic effects of exogenously infused MSCs might also root from healthy MSC-induced MM cell death/apoptosis [5]. However, the underlying crosstalk between MSCs and MM cells in vitro and in vivo remains unknown. The execution of programmed cell death is a process triggered through many factors, such as radiation, chemotherapeutic drugs, and apoptotic signaling, which occurs via intrinsic and extrinsic pathways. Both pathways stimulate an intracellular cascade of events leading to cell death. The intrinsic pathway is initiated by mitochondria, whereas the extrinsic pathway is activated through death receptors that engage their respective ligands on the surface membrane of target cells. Fas (DR2/CD95/Apo-1) is a type I cell membrane protein with an extracellular domain that binds Fas ligand (Fas-L) and a cytoplasmic domain that transduces the death signal [19, 20]. Fas-L (CD95L/CD178/Apo-1 L) is a type II cell membrane protein belonging to the TNF family, which is inducibly expressed in lymphocytes and constitutively expressed in cells present in immuneprivileged organs [21, 22]. Fas-L interacts with its receptor, Fas, triggering a cascade of subcellular events culminating in apoptotic cell death [23]. Although Fas/Fas-L interactions play an important role in inducing cell apoptosis, it remained unclear whether Fas/Fas-L is involved in the inhibitory effects of exogenously infused MSCs on MM cells. The purpose of the present study was therefore to determine whether MSCs exert apoptosis inducing effects on MM cells in vitro and in vivo through altering Fas/Fas-L expression.

MM is a malignancy of antibody-secreting plasma cells, where B-cell plasmacytomas stimulate osteoclast activity, and hence bone resorption, resulting in progressive osteolytic lesions [18]. Based on studies concerning the pathogenic role of autoantibodies in MM diseases, recent advances in this field suggest a more central role for B cells in the maintenance of the disease process beyond their roles as precursors for (auto) antibody-producing plasma cells [31]. Particularly, a number of surface molecules and subsequent downstream signaling pathways are involved in the regulation of MM-related bone destroying events, in which bone resorption and formation are no longer balanced as a consequence of the increased activity of osteoclasts, but rather the osteoblast activity is reduced, leading to an uncoupled, or severely imbalanced, bone remodeling process [2]. Clinical data have shown that MM patients with advanced bone lesions might show a reduction of bone formation markers, such as alkaline phosphatase and osteocalcin, together with increased bone resorption markers, such as receptor activator of nuclear factor κB ligand (RANKL) and C-terminal cross-linked telopeptide of type I collagen [32]. Similarly, marked osteoblastopenia and reduced bone formation have also been reported in murine models of MM bone disease [33]. These studies demonstrate that MM cells suppress osteoblast formation and differentiation, and consequently inhibit bone formation.

Recent mounting evidence indicates that MM cells suppress osteoblastogenesis through contact-dependent cell—cell interaction [7, 34] and the production of osteoblastinactivating factors including Wnt inhibitors, such as dickkopf-1 [10] and secreted frizzled-related protein 2 [35], and cytokines, such as CCL3 (also known as macrophage inflammatory protein-1 alpha) [11], hepatocyte growth factor, and IL-3/6 [18]. Osteolytic lesions in MM are only observed adjacent to intramedullary plasma cell foci or plasmacytomas, supporting the idea that MM cells might secrete factors that promote the activation of osteoclasts and the inactivation of osteoblast function to replace bone loss [36]. More effective approaches to cure MM-related bone disease, in addition to the correction of osteoblast function, should therefore be reflected in therapeutic modalities aimed at inducing MM cell death.

Researchers in the stem cell field are working to translate the knowledge gained from stem cell biology and function into therapeutic breakthroughs and applications. It is well known that osteoblasts originate primarily from MSCs and are responsible for bone matrix synthesis through the secretion of collagen, which forms strands called osteoid [37]. Osteoclast activity is regulated through the expression of cytokines, such as receptor activator of RANKL, which activates osteoclast differentiation, and osteoprotegerin, which acts as a decoy receptor and inhibits RANKL [38]. Based on this knowledge, MSC-based cytotherapy has established a novel concept for the treatment of MM-related bone disease [39]. Recently, Li and colleagues demonstrated that both systemic and intrabone cytotherapeutic strategies were effective and clinically applicable for treating MM-related bone disease [15], where weekly systemic injections of MSCs restrained MM disease progression through the ability of MSCs to traffic to myelomatous bone and survive for a short period of time [5]. Intrabone injections of MSCs, however, not only inhibited tumor growth in the bone with active MM but also effectively promoted bone formation during disease, remission and delayed MM relapse. Whether MSCs inhibit or promote cancer growth has developed into a controversy reflected in concern over the use of MSCs, which exhibit a propensity to home to tumors. Once resident in the tumor microenvironment, these cells support tumor growth and spread [14], although the ability of cultured MSCs to support long-term growth of primary MM cells is often limited and not reproducible [40, 41]. Therefore, understanding the in vivo milieu in which MSCs either inhibit or enhance MM cell survival and metastasis is crucial both to safely develop MSCs as a therapeutic tool and to advance our understanding of the role of tumor stroma in carcinogenesis [16, 17]. Moreover, there is still not a general consensus of what defines these MSCs; the polarization of MSCs into a proinflammatory or an immunosuppressive phenotype showing reversed effects on tumor growth has been observed [17, 42].

Recent findings suggest that the overexpression of growth differentiation factor 15 in bone marrow MSCs occurs widely in patients with MM. Tumor microenvironment-derived growth differentiation factor 15 is a key survival and chemoprotective factor for MM cells, indicating that the behavior of MSCs might be principally determined by the surrounding environment [43]. The two side effects of MSCs on MM cells identified from previous studies are therefore basically acceptable.

Previous reports have indicated that murine and human MSCs promote breast and coronal cancer growth and metastasis [44, 45]. Interestingly, Ma and colleagues showed that human umbilical cord MSCs significantly inhibited the growth of breast cancer cells in vitro and in vivo [46]. Furthermore, the ability of cytotherapy through placenta-derived adherent cells to impact bone remodeling and increase bone formation in nonmyelomatous SCID-rab mice has been demonstrated [15]. Intralesional mesenchymal cell cytotherapy also resulted in inhibiting growth of H929 MM cells and primary MM cells categorized through global gene expression as high risk. Moreover, placenta-derived adherent cells had no effect on the subcutaneous growth of H929 MM cells in SCID mice, and did not confer a growth advantage to MM cells co-cultured with placenta-derived adherent cells or supportive MSCs [47]. Recently, adipose derived MSCs, engineered to express the pro-apoptotic ligand TRAIL (also known as TNFSF10), killed MM cells and migrated towards MM cells in vitro [48].

It has been well recognized that MSC therapy potentially offers novel therapeutic modalities that are translatable for clinical treatment of a large variety of pathological conditions or diseases [49]. This development is also true for clinically managing and combating cancer, as MSCs play a central role in the pathogenesis and progression of tumors [5, 50]. MSC administration thus reduces solid tumor growth in mice due to an inhibition of tumor cell proliferation, probably resulting from deep modifications of the tumor angiogenesis, regardless of the tumor model and mode of MSC injection [51]. Clinically, current evidence suggests that cytotherapy markedly increases the proportion of MSCs in bone of MM patients, at least for a short period of time [5, 15]. As deduced from in vitro studies, during this short time, the injected MSCs probably interact with endogenous osteoblast precursors and secrete factors that induce their differentiation into bone-building osteoblasts, while simultaneously directly interactions with osteoclast precursors to secrete factors that attenuate the formation of boneresorbing osteoclasts [15]. Notably, similar to osteoblasts, MSCs might produce a high level of decorin protein, which inhibits osteoclast formation and promotes osteoblast differentiation [8]. Following the identification of the potential for MSCs to enhance engraftment of hematopoietic stem cells, increase osteoblast activity and suppress osteoclast activity [52], MSCs recruited hematopoietic elements that inhibit inflammatory conditions typically associated with MM growth in bone [15]. Along with recent findings in this field [17, 42], it is speculated that MM progression is restrained, directly and indirectly, through anti-inflammatory factors produced by the injected MSCs or endogenous cells recruited to myelomatous bone after cytotherapy. The findings that MSCs express high levels of anti-inflammatory and antineoplastic factors, such as SERPINF1 and decorin, support this concept [5]. Decorin also attenuates MM cell growth [5]. Although certain soluble factors produced by MSCs might mediate part of their therapeutic activities, cytotherapy at a remote site (subcutaneous) was found to have no effect on MM bone disease or growth [15], suggesting that MSCs must be present in bone marrow to elicit their antimyeloma effects. Indeed, only MSCs injected directly into bone might efficiently induce an antimyeloma environment. Systemically injected MSCs significantly promote bone formation or restrain MM growth because relatively few of those MSCs can transmigrate and traffic to bone [5]. Recent results, however, also suggest that MSCs might be attracted to bone through MM cells or conditions induced through MM or melphalan treatment. More importantly, MSCs might be cleared in various tissues, but exhibit higher survival rates in the implanted bone or lymph nodes and therefore could be detected in these tissues at 2 to 3 days after intravenous or intracardiac injections, respectively [5]. The accumulation of MSCs in lymph nodes, however, might partially explain their immunomodulatory properties. In fact, evidence suggests that intravenously injected MSCs might localize in the lymph nodes of experimental mouse models of autoimmunity [53, 54]. This body of work might also explain the fewer numbers and smaller sizes of cancroid pearls in the neck and root tail of the MSC-treated MM mice in the present study.

Recent studies have revealed that exogenously injected MSCs were not detectable in vivo for long periods of time; the majority of these cells disappeared within 3 to 5 weeks [15, 55]. Clinically, this phenomenon might be advantageous because it limits the duration of the intervention, and these observations support the notion that most of their activities are mediated through the touch-and-go mechanisms of bystander cells, although proof of such evanescence is thus far not well defined [5, 56]. In support of using allogeneic MSCs for MM, Li and colleagues recently demonstrated that intralesionally injected human placenta mesenchymal cells exert similar therapeutic effects in SCID-rab mice [15]. Together, these studies raise an intriguing possibility: if we could understand how MSCs induce MM cell death, then perhaps we could exogenously manipulate MSCs to effectively manage MM and saved a large number of lives. An important, yet unelucidated, question raised by our study is whether a majority of MSCs transmigrate to the myelomatous bone to kill MM cells after intravenous injection, or traffic to lymph nodes to exert inhibitory effects on MM cells via the secretion of anti-inflammatory factors.

The potential role of molecules involved in altered B-cell longevity, particularly those involved in apoptosis (for example, Fas/Fas-L modulators), and those that might alter activation thresholds of B cells in the development of autoimmunity, might contribute to the clinical management of MM [27, 31]. Unfortunately, however, relatively little is known about this issue. Recently, a number of studies have reported the effects of the Fas/Fas-L pathway on fluoride-induced or melatonininduced cell apoptosis [57, 58].

Although Mazar and colleagues detected Fas expression on MSCs, stimulation of Fas with different concentrations of anti-Fas antibody did not result in any apoptotic response [23]. Previously demonstrated that caspase-8 deficiency resulted in the inhibition of apoptosis of Jurkat cells, and blocking with Fas Fc protein prevented bone marrow MSC-induced apoptosis in 80% [23]. Other studies have shown that the transformation of the intracellular domain of Fas protein expressed in human MSCs prevents the trimerization of the receptor and blocks the activation of apoptotic pathway activation [59]. For a further discussion of such mechanisms, see [60]-[62].

RELATED ART REFERENCES

Following publications are the related art for the background of this disclosure. The one digit or two digit numbers in the box brackets before each reference, i.e. [1] to [62], correspond to the numbers in the box brackets used in the other parts of this disclosure.

[1] Bergsagel P L, Kuehl W M: Molecular pathogenesis and a consequent classification of multiple myeloma. J Clin Oncol 2005, 23:6333-6338.

[2] Yaccoby S: Advances in the understanding of myeloma bone disease and tumour growth. Br J Haematol 2010, 149:311-321.

[3] Giuliani N, Rizzoli V, Roodman G D: Multiple myeloma bone disease: pathophysiology of osteoblast inhibition. Blood 2006, 108:3992-3996.

[4] Walker R, Barlogie B, Haessler J, Tricot G, Anaissie E, Shaughnessy J D Jr, Epstein J, van Hemert R, Erdem E, Hoering A, Crowley J, Ferris E, Hollmig K, van Rhee F, Zangari M, Pineda-Roman M, Mohiuddin A, Yaccoby S, Sawyer J, Angtuaco E J: Magnetic resonance imaging in multiple myeloma: diagnostic and clinical implications. J Clin Oncol 2007, 25:1121-1128.

[5] Li X, Ling W, Khan S, Yaccoby S: Therapeutic effects of intrabone and systemic mesenchymal stem cell cytotherapy on myeloma bone disease and tumor growth. J Bone Miner Res 2012, 27:1635-1648.

[6] Jemal A, Graubard B I, Devesa S S, Flegal K M: The association of blood lead level and cancer mortality among whites in the United States. Environ Health Perspect 2002, 110:325-329.

[7] Giuliani N, Colla S, Morandi F, Lazzaretti M, Sala R, Bonomini S, Grano M, Colucci S, Svaldi M, Rizzoli V: Myeloma cells block RUNX2/CBFA1 activity in human bone marrow osteoblast progenitors and inhibit osteoblast formation and differentiation. Blood 2005, 106:2472-2483.

[8] Li X, Pennisi A, Yaccoby S: Role of decorin in the antimyeloma effects of osteoblasts. Blood 2008, 112:159-168.

[9] Giuliani N, Mangoni M, Rizzoli V: Osteogenic differentiation of mesenchymal stem cells in multiple myeloma: identification of potential therapeutic targets. Exp Hematol 2009, 37:879-886.

[10] Yaccoby S, Ling W, Zhan F, Walker R, Barlogie B, Shaughnessy J D Jr: Antibody-based inhibition of DKK1 suppresses tumor-induced bone resorption and multiple myeloma growth in vivo. Blood 2007, 109:2106-2111.

[11] Vallet S, Pozzi S, Patel K, Vaghela N, Fulciniti M T, Veiby P, Hideshima T, Santo L, Cirstea D, Scadden D T, Anderson K C, Raje N: A novel role for CCL3 (MIP-1alpha) in myeloma-induced bone disease via osteocalcin downregulation and inhibition of osteoblast function. Leukemia 2011, 25:1174-1181.

[12] Gasparetto C: Stem cell transplantation for multiple myeloma. Cancer Control 2004, 11:119-129.

[13] Suzuki K, Sun R, Origuchi M, Kanehira M, Takahata T, Itoh J, Umezawa A, Kijima H, Fukuda S, Saijo Y: Mesenchymal stromal cells promote tumor growth through the enhancement of neovascularization. Mol Med 2011, 17:579-587.

[14] Klopp A H, Gupta A, Spaeth E, Andreeff M, Marini F 3rd: Concise review: Dissecting a discrepancy in the literature: do mesenchymal stem cells support or suppress tumor growth? Stem Cells 2011, 29:11-19.

[15] Li X, Ling W, Pennisi A, Wang Y, Khan S, Heidaran M, Pal A, Zhang X, He S, Zeitlin A, Abbot S, Faleck H, Hariri R, Shaughnessy J D Jr, van Rhee F, Nair B, Barlogie B, Epstein J, Yaccoby S: Human placenta-derived adherent cells prevent bone loss, stimulate bone formation, and suppress growth of multiple myeloma in bone. Stem Cells 2011, 29:263-273.

[16] Chen L, Wang S, Zhou Y, Wu X, Entin I, Epstein J, Yaccoby S, Xiong W, Barlogie B, Shaughnessy J D Jr, Zhan F: Identification of early growth response protein 1 (EGR-1) as a novel target for JUN-induced apoptosis in multiple myeloma. Blood 2010, 115:61-70.

[17] Waterman R S, Henkle S L, Betancourt A M: Mesenchymal stem cell 1 (MSC1)-based therapy attenuates tumor growth whereas MSC2-treatment promotes tumor growth and metastasis. PLoS One 2012, 7:e45590.

[18] Gunn W G, Conley A, Deininger L, Olson S D, Prockop D J, Gregory C A: A crosstalk between myeloma cells and marrow stromal cells stimulates production of DKK1 and interleukin-6: a potential role in the development of lytic bone disease and tumor progression in multiple myeloma. Stem Cells 2006, 24:986-991.

[19] Peter M E, Budd R C, Desbarats J, Hedrick S M, Hueber A O, Newell M K, Owen L B, Pope R M, Tschopp J, Wajant H, Wallach D, Wiltrout R H, Zörnig M, Lynch D H: The CD95 receptor: apoptosis revisited. Cell 2007, 129:447-450.

[20] Strasser A, Jost P J, Nagata S: The many roles of Fas receptor signalling in the immune system. Immunity 2009, 30:180-192.

[21] Suda T, Takahashi T, Golstein P, Nagata S: Molecular cloning and expression of the Fas ligand, a novel member of the tumor necrosis factor family. Cell 1993, 75:1169-1178.

[22] Lettau M, Paulsen M, Kabelitz D, Janssen O: Storage, expression and function of Fas ligand, the key death factor of immune cells. Curr Med Chem 2008, 15:1684-1696.

[23] Mazar J, Thomas M, Bezrukov L, Chanturia A, Pekkurnaz G, Yin S, Kuznetsov S A, Robey P G, Zimmerberg J: Cytotoxicity mediated by the Fas ligand (FasL)-activated apoptotic pathway in stem cells. J Biol Chem 2009, 284:22022-22028.

[24] LeBlanc R, Catley L P, Hideshima T, Lentzsch S, Mitsiades C S, Mitsiades N, Neuberg D, Goloubeva O, Pien C S, Adams J, Gupta D, Richardson P G, Munshi N C, Anderson K C: Proteasome inhibitor PS-341 inhibits human myeloma cell growth in vivo and prolongs survival in a murine model. Cancer Res 2002, 62:4996-5000.

[25] Liu Y, Wang L, Kikuiri T, Akiyama K, Chen C, Xu X, Yang R, Chen W, Wang S, Shi S: Mesenchymal stem cell-based tissue regeneration is governed by recipient T lymphocytes via IFN-γ and TNF-α. Nat Med 2011, 17:1594-1601.

[26] Oyajobi B O, Franchin G, Williams P J, Pulkrabek D, Gupta A, Munoz S, Grubbs B, Zhao M, Chen D, Sherry B, Mundy G R: Dual effects of macrophage inflammatory protein-1 alpha on osteolysis and tumor burden in the murine 5TGM1 model of myeloma bone disease. Blood 2003, 102:311-319.

[27] Akiyama K, Chen C, Wang D, Xu X, Qu C, Yamaza T, Cai T, Chen W, Sun L, Shi S: Mesenchymal-stem-cell-induced immunoregulation involves FAS-ligand-/FAS-mediated T cell apoptosis. Cell Stem Cell 2012, 10:544-555.

[28] Musto P, D'Auria F: Melphalan: old and new uses of a still master drug for multiple myeloma. Expert Opin Investig Drugs 2007, 16:1467-1487.

[29] Zhang Q, Shi S, Liu Y, Uyanne J, Shi Y, Shi S, Le A D: Mesenchymal stem cells derived from human gingiva are capable of immunomodulatory functions and ameliorate inflammation-related tissue destruction inexperimental colitis. J Immunol 2009, 183:7787-7798.

[30] Sun L Y, Zhou K X, Feng X B, Zhang H Y, Ding X Q, Jin O, Lu L W, Lau C S, Hou Y Y, Fan L M: Abnormal surface markers expression on bone marrow CD34+ cells and correlation with disease activity in patients with systemic lupus erythematosus. Clin Rheumatol 2007, 26:2073-2079.

[31] Dörner T, Lipsky P E: Signalling pathways in B cells: implications for autoimmunity. Curr Top Microbiol Immunol 2006, 305:213-240.

[32] Vejlgaard T, Abildgaard N, Jans H, Nielsen J L, Heickendorff L: Abnormal bone turnover in monoclonal gammaopathy of undetermined significance: analyses of type I collagen telopeptide, osteocalcin, bone-specific alkaline phosphatase and propeptides of type I and type III procollagens. Eur J Haematol 1997, 58:104-108.

[33] Hjorth-Hansen H, Seifert M F, Börset M, Aarset H, Ostlie A, Sundan A, Waage A: Marked osteoblastopenia and reduced bone formation in a model of multiple myeloma bone disease in severe combined immunodeficiency mice. J Bone Miner Res 1999, 14:256-263.

[34] Pennisi A, Ling W, Li X, Khan S, Shaughnessy J D Jr, Barlogie B, Yaccoby S: The ephrinB2/EphB4 axis is dysregulated in osteoprogenitors from myeloma patients and its activation affects myeloma bone disease and tumor growth. Blood 2009, 114:1803-1812.

[35] Oshima T, Abe M, Asano J, Hara T, Kitazoe K, Sekimoto E, Tanaka Y, Shibata H, Hashimoto T, Ozaki S, Kido S, Inoue D, Matsumoto T: Myeloma cells suppress bone formation by secreting a soluble Wnt inhibitor, sFRP-2. Blood 2005, 106:3160-3165.

[36] Bataille R, Manolagas S C, Berenson J R: Pathogenesis and management of bone lesions in multiple myeloma. Hematol Oncol Clin North Am 1997, 11:349-361.

[37] Gregory C A, Gunn W G, Reyes E, Smolarz A J, Munoz J, Spees J L, Prockop D J: How Wnt signaling affects bone repair by mesenchymal stem cells from the bone marrow. Ann NY Acad Sci 2005, 1049:97-106.

[38] Glass D A, Patel M S, Kassenty G: A new insight into the formation of osteolytic lesions in multiple myeloma. N Engl J Med 2003, 349:2479-2480.

[39] Fu J, Wang P, Zhang X, Ju S, Li J, Li B, Yu S, Zhang J, Zhang X: Myeloma cells inhibit osteogenic differentiation of mesenchymal stem cells and kill osteoblasts via TRAIL-induced apoptosis. Arch Med Sci 2010, 6:496-504.

[40] Mitsiades C S, McMillin D W, Klippel S, Hideshima T, Chauhan D, Richardson P G, Munshi N C, Anderson K C: The role of the bone marrow microenvironment in the pathophysiology of myeloma and its significance in the development of more effective therapies. Hematol Oncol Clin North Am 2007, 21:1007-1034. vii-viii.

[41] Wang X, Zhang Z, Yao C: Survivin is upregulated in myeloma cell lines cocultured with mesenchymal stem cells. Leuk Res 2010, 34:1325-1329.

[42] Coffelt S B, Marini F C, Watson K, Zwezdaryk K J, Dembinski J L, LaMarca H L, Tomchuck S L, Honer Z U, Bentrup K, Danka E S, Henkle S L, Scandurro A B: The pro-inflammatory peptide LL-37 promotes ovarian tumor progression through recruitment of multipotent mesenchymal stromal cells. Proc Natl Acad Sci USA 2009, 106:3806-3811.

[43] Corre J, Labat E, Espagnolle N, Hébraud B, Avet-Loiseau H, Roussel M, Huynh A, Gadelorge M, Cordelier P, Klein B, Moreau P, Facon T, Fournié J J, Attal M, Bourin P: Bioactivity and prognostic significance of growth differentiation factor GDF15 secreted by bone marrow mesenchymal stem cells in multiple myeloma. Cancer Res 2012, 72:1395-1406.

[44] Shinagawa K, Kitadai Y, Tanaka M, Sumida T, Kodama M, Higashi Y, Tanaka S, Yasui W, Chayama K: Mesenchymal stem cells enhance growth and metastasis of colon cancer. Int J Cancer 2010, 127:2323-2333.

[45] Albarenque S M, Zwacka R M, Mohr A: Both human and mouse mesenchymal stem cells promote breast cancer metastasis. Stem Cell Res 2011, 7:163-171.

[46] Ma Y, Hao X, Zhang S, Zhang J: The in vitro and in vivo effects of human umbilical cord mesenchymal stem cells on the growth of breast cancer cells. Breast Cancer Res Treat 2012, 133:473-485.

[47] Caligaris-Cappio F, Bergui L, Gregoretti M G, Gaidano G, Gaboli M, Schena M, Zallone A Z, Marchisio P C: Role of bone marrow stromal cells in the growth of human multiple myeloma. Blood 1991, 77:2688-2693.

[48] Ciavarella S, Grisendi G, Dominici M, Tucci M, Brunetti O, Dammacco F, Silvestris F: In vitro anti-myeloma activity of TRAIL-expressing adipose-derived mesenchymal stem cells. Br J Haematol 2012, 157:586-598.

[49] Chen F M, Zhao Y M, Jin Y, Shi S: Prospects for translational regenerative medicine. Biotechnol Adv 2012, 30:658-672.

[50] Gomes C M: The dual role of mesenchymal stem cells in tumor progression. Stem Cell Res Ther 2013, 4:42.

[51] Kéramidas M, de Fraipont F, Karageorgis A, Moisan A, Persoons V, Richard M J, Coll J L, Rome C: The dual effect of mesenchymal stem cells on tumour growth and tumour angiogenesis. Stem Cell Res Ther 2013, 4:41.

[52] Prather W R, Toren A, Meiron M: Placental-derived and expanded mesenchymal stromal cells (PLX-I) to enhance the engraftment of hematopoietic stem cells derived from umbilical cord blood. Expert Opin Biol Ther 2008, 8:1241-1250.

[53] Zappia E, Casazza S, Pedemonte E, Benvenuto F, Bonanni I, Gerdoni E, Giunti D, Ceravolo A, Cazzanti F, Frassoni F, Mancardi G, Uccelli A: Mesenchymal stem cells ameliorate experimental autoimmune encephalomyelitis inducing T-cell anergy. Blood 2005, 106:1755-1761.

[54] Parekkadan B, Tilles A W, Yarmush M L: Bone marrow-derived mesenchymal stem cells ameliorate autoimmune enteropathy independently of regulatory T cells. Stem Cells 2008, 26:1913-1919.

[55] Prockop D J: Repair of tissues by adult stem/progenitor cells (MSCs): controversies, myths, and changing paradigms. Mol Ther 2009, 17:939-946.

[56] Uccelli A, Moretta L, Pistoia V: Mesenchymal stem cells in health and disease. Nat Rev Immunol 2008, 8:726-736.

[57] Xu B, Xu Z, Xia T, He P, Gao P, He W, Zhang M, Guo L, Niu Q, Wang A: Effects of the Fas/Fas-L pathway on fluoride-induced apoptosis in SH-SY5Y cells. Environ Toxicol 2011, 26:86-92.

[58] García-Santos G, Martin V, Rodríguez-Blanco J, Herrera F, Casado-Zapico S, Sánchez-Sánchez A M, Antolín I, Rodríguez C: Fas/Fas ligand regulation mediates cell death in human Ewing's sarcoma cells treated with melatonin. Br J Cancer 2012, 106:1288-1296.

[59] O'Connell J, Houston A, Bennett M W, O'Sullivan G C, Shanahan F: Immune privilege or inflammation? Insights into the Fas ligand enigma. Nat Med 2012, 7:271-274. 2001.

[60] Yang X, Yang C, Shao K, Ye X, Meng H, Zhou Y, Qian W: Refractory multiple myeloma treated with homoharringtonine: report of two cases.

Ann Hematol 2007, 86:919-921.

[61] Lou Y J, Qian W B, Jin J: Homoharringtonine induces apoptosis and growth arrest in human myeloma cells. Leuk Lymphoma 2007, 48:1400-1406.

[62] Khakoo A Y, Pati S, Anderson S A, Reid W, Elshal M F, Rovira I I, Nguyen A T, Malide D, Combs C A, Hall G, Zhang J, Raffeld M, Rogers T B, Stetler-Stevenson W, Frank J A, Reitz M, Finkel T: Human mesenchymal stem cells exert potent antitumorigenic effects in a model of Kaposi's sarcoma. J Exp Med 2006, 203:1235-1247.

The contents of above publications are incorporated herein in their entirety.

SUMMARY

This disclosure relates in general to a stem cell treatment. This disclosure further relates to a stem cell treatment using a composition comprising a stem cell with highly expressed Fas-L. This disclosure also relates to a composition comprising stem cells having highly expressed Fas-L. This disclosure also relates to preparation of a composition comprising stem cells having highly expressed Fas-L. This disclosure also relates to preparation of a composition comprising stem cells having highly expressed Fas-L by using a salicylate. An example of salicylate may be aspirin. This disclosure further relates to a stem cell treatment of multiple myeloma. This disclosure also relates to a stem cell treatment of an inflammatory disease and/or autoimmune disease.

In one example, a composition may comprise an isolated stem cell having highly expressed Fas ligand (Fas-L). The isolated stem cell may be mesenchymal stem cell having highly expressed Fas-L. In another example, the isolated stem cell may be a bone marrow derived mesenchymal stem cell having highly expressed Fas-L. Yet, in another example, the stem cell may be a gingiva derived mesenchymal stem cell having highly expressed Fas-L.

In one example, a preparation method may be a method for preparing a composition suitable for a stem cell treatment of a mammal. For example, the preparation method may comprise obtaining a tissue comprising a stem cell, treating the tissue to activate or increase level of Fas-L expression, and thereby obtaining a treated stem cell having highly expressed Fas-L, and preparing a composition comprising the treated stem cell having highly expressed Fas-L. The treating the tissue may comprise separating the tissue into cells, sorting the stem cell, and treating the stem cell. In another example, the treating the tissue may comprise treating the tissue, separating the tissue into cells, and sorting the stem cell.

In one exemplary preparation method, the tissue may be treated by using a salicylate. For example, the treating the tissue may comprise separating the tissue into cells, sorting the stem cell, and treating the stem cell by using a salicylate. In another example, the treating the tissue may comprise treating the tissue by using salicylate, separating the tissue into cells, and sorting the stem cell. In one example, the stem cell may be treated by preparing a solution comprising salicylate and treating the tissue using the solution comprising salicylate. The salicylate concentration of the solution may vary in the range of 1 µg/ml to 1,000 µg/ml. The salicylate concentration of the solution may also vary in the range of 5 µg/ml to 200 µg/ml. The salicylate concentration of the solution may also vary in the range of 25 µg/ml to 100 µg/ml. The tissue may be treated for a duration varying in the range of 1 hour to 100 days. The tissue may be treated for a duration varying in the range of 1 day to 20 days. The tissue may be treated for a duration varying in the range of 3 hour to 10 days. The treating the tissue may further comprise separating the salicylate from the tissue and thereby preparing a substantially salicylate free composition comprising the treated stem cell having highly expressed Fas-L. For the preparation methods, an example of the salicylate may be aspirin.

For the preparation methods, the tissue may comprise a mesenchymal stem cell (MSC). Also, for the preparation methods, the tissue may comprise a bone marrow tissue, a gingival tissue or combinations thereof. The MSCs may be bone marrow derived MSCs, gingiva derived MSCs, or combinations thereof.

In one example, a treatment method may comprise treating a mammal using the composition comprising the stem cell having highly expressed Fas-L. For example, the treatment method may comprise treating the mammal by using the composition comprising the stem cell having highly expressed Fas-L to treat the mammal that has multiple myeloma (MM). This treatment may inhibit at least tumor growth. This treatment may increase survival rate of the mammal that has MM. Treating the mammal may comprise using the composition comprising the stem cell having highly expressed Fas-L to treat the mammal that has an inflammatory and/or autoimmune disease. Examples of the inflammatory and/or autoimmune disease may be graft-versus-host disease (GvHD), diabetes, rheumatoid arthritis (RA), autoimmune encephalomyelitis, systemic lupus erythematosus (SLE), multiple sclerosis (MS), systemic sclerosis, osteoporosis, periodontitis, inflammatory bowel disease (IBD), alimentary tract mucositis induced by chemotherapy, alimentary tract mucositis induced by radiotherapy, or sepsis. The treatment may increase survival rate of the mammal that has an inflammatory and/or autoimmune disease. For the treatment method, the stem cell may comprise an MSC. For example, the MSC may comprise a bone marrow derived MSC. In another example, the MSC may comprise a gingiva derived MSC.

Any combination of inventive features disclosed above may be possible and thereby within scope of this disclosure. For example, a method of preparing a composition suitable for a stem cell treatment of a mammal, wherein the preparation method may comprise obtaining a tissue comprising a stem cell, separating the tissue into cells, sorting the stem cell, treating the stem cell, and preparing a composition comprising the treated stem cell having highly expressed Fas-L. In another example, a method of preparing a composition suitable for a stem cell treatment of a mammal, wherein the preparation method may comprise obtaining a tissue comprising a stem cell, treating the tissue, separating the treated tissue into cells, sorting the stem cell, and preparing a composition comprising the treated stem cell having highly expressed Fas-L. In these examples, the tissue or a stem cell may be treated by using a salicylate. An example of a salicylate may be aspirin. In these examples, the using a salicylate may comprise preparing a solution comprising a salicylate at a predetermined salicylate concentration for a predetermined salicylate treatment duration. The predetermined salicylate concentration may vary in the range of 1 μg/ml to 1,000 μg/ml, or in the range of 5 μg/ml to 200 μg/ml, or in the range of 25 μg/ml to 100 μg/ml. The predetermined salicylate treatment duration may vary in the range of 1 hour to 100 days, or in the range of 1 day to 20 days, or in the range of 3 days to 10 days. In these examples, an example of a salicylate may be aspirin. In these examples, the tissue may comprise a bone marrow tissue, a gingival tissue, or combinations thereof. In these examples, the stem cell may comprise an MSC. Examples of MSC may be bone marrow derived MSCs, gingiva derived MSCs, or combinations thereof. The composition thereby prepared may be used in a treatment of a mammal that has multiple myeloma, an inflammatory and/or autoimmune disease. Examples of the inflammatory and/or autoimmune diseases may be graft-versus-host disease (GvHD), diabetes, rheumatoid arthritis (RA), autoimmune encephalomyelitis, systemic lupus erythematosus (SLE), multiple sclerosis (MS), systemic sclerosis, osteoporosis, periodontitis, inflammatory bowel disease (IBD), alimentary tract mucositis induced by chemotherapy, alimentary tract mucositis induced by radiotherapy, or sepsis.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIGS. 1A-1H illustrate the effect of mesenchymal stem cell infusion in multiple myeloma model mice. FIG. 1A illustrates an experimental protocol of multiple myeloma (MM) cell and mesenchymal stem cell (MSC) injection and the design of lymphocyte Peyer's patch adhesion molecule (LPAM) administration. FIG. 1B shows six-week survival rates of animals in different groups (for each group, n=14). The survival rate in the non-treated MM model group was dramatically decreased after about 3 weeks. The MSC and L-PAM groups had almost the same survival rate, but were higher than the MM group (P<0.05). Data shown as mean±standard deviation (SD) of three parallel experiments. *P<0.05 versus MM group. FIGS. 1C-1D show a comparison of clinical findings in each group. FIG. 1C includes representative photographs of typical cancroid pearls in the base of the tail (bar=about 5 mm). In FIG. 1D the number (left) and size (right) of cancroid pearls in the neck, root of tail and abdominal cavity are shown as column graphs. Data shown as mean±SD for three parallel experiments. *P<0.05 versus MSC group; #P<0.05 versus L-PAM group. FIGS. 1E and 1F present a comparison of bone resorption in lumbus and collum femoris in each group. FIG. 1E presents radiographs of lumbus and collum femoris at about 3 weeks after MM cell injection, and the bone density in each group was analyzed. FIG. 1F presents graphs with data shown as mean±SD for four parallel experiments. *P<0.05 versus MM group; #P<0.05 versus L-PAM group. FIGS. 1G and 1H illustrate myeloma cell metastasis in the lungs and kidneys in each group. In FIG. 1G, the left panels depict light micrographs of the lungs and kidneys (hematoxylin and eosin staining, bar=about 100 μm). Con: control. FIG. 1H present data shown as mean±SD for three parallel experiments. *P<0.05 versus MSC group.

FIG. 2A is a graph showing multiplication of multiple myeloma (MM) cells under co-culture with mesenchymal stem cells (MSCs). FIG. 2B presents Western blot analyses of apoptosis markers. Expression levels of cleaved caspase-3 and caspase-8 in MM cells with or without co-culture with MSCs were analyzed through western blotting at about 0 hour, about 6 hours, about 12 hours, and about 24 hours (lower table arranged to numerical value from upper data). FIGS. 2C-2D illustrate apoptotic analysis through fluorescence-activated cell sorting (FACS) (x axis, Annexin V; y axis, 7AAD-positive cells). Apoptosis of MM cells with or without co-culture with MSCs was detected and quantified through FACS at about 0 hour, about 6 hours, about 12 hours, and about 24 hours (lower table arranged from upper data). Data presented as mean±standard deviation (SD) for two parallel experiments. #P <0.05 versus the control group (Cont.). FIGS. 2E-2F illustrate rate of apoptotic MM cells under co-culture with MSCs. The microscope pictures in FIG. 2E represent typical reactions of MM cells in fluorescence staining, where MM cells were prestained for carboxyfluorescein diacetate, succinimidyl ester (CFSE; green) and apoptosis markers using Annexin V and 7AAD (red). The table in FIG. 2F is arranged to present numerical value from data derived from FIG. 2E. Data presented as mean±SD for two parallel experiments. #P<0.05 versus the control group (Cont.). DAPI, 4',6-diamidino-2-phenylindole.

FIG. 3A illustrates multiplication of multiple myeloma (MM) cells under different co-culture conditions with mesenchymal stem cells (MSCs) (Cont., MM single culture; C-medium, MM culture with conditioned medium from MSC culture; Trans-well, indirect co-culture between MM and MSC; Co-cul, direct culture between MM and MSC). Each data point represents the mean±standard deviation (SD) of two parallel experiments. #P<0.05 versus the control group (Cont.). FIG. 3B presents Western blotting analyses of the expression levels of Fas and Fas ligand (Fas-L) in MM cells and MSCs under co-culture condition for about 0 hour, about 6 hours, about 12 hours, and about 24 hours. FIGS. 3C-3F illustrate the rates of Fas-positive or Fas-L-positive cells were determined through immunofluorescence staining. In FIGS. 3C-3D, MM cells were prestained for carboxyfluorescein diacetate, succinimidyl ester (CFSE; green) and then post-stained for Fas (red). In FIGS. 3E-3F, MSCs were stained for Scar-1 (green) and subsequently stained for Fas-L (red). Bar=about 300 μm. Numbers of Fas-positive MM cells and Fas-L-positive MSCs are shown. Data presented as the mean±SD for two parallel experiments. #P<0.05 versus the control group (Cont.). DAPI, 4',6-diamidino-2-phenylindole.

FIG. 4A presents a comparison of Fas ligand (Fas-L) expression in mesenchymal stem cells (MSCs) after aspirin treatment. FIG. 4B shows multiplication of multiple myeloma (MM) cells under co-culture condition with MSCs that express different levels of Fas-L. For the graph in FIG. 4B, the number of MM co-cultured without MSCs (Cont.), with normal MSCs (Co-cul), with MSCs from generalized lymphoproliferative disease mice (Co-cul(gld)) or with MSCs treated with any aspirin (Co-cul(Asp)) were counted after about 0 hour, about 6 hours, about 12 hours, or about 24 hours. FIGS. 4C-4D illustrate apoptotic analysis of MM cells under co-culture condition with MSCs expressing different levels of Fas-L (detected and quantified through fluorescence-activated cell sorting (FACS): x axis, Annexin V; y axis, 7AAD-positive cells). Data presented as mean±standard deviation (SD) for two parallel experiments. #$P<0.05$ versus Con. FIG. 4E presents expression levels of cleaved caspase-3 in MM cells with or without co-cultured MSCs (expressing different levels of Fas-L) at about 0 hour, about 6 hours, about 12 hours, and about 24 hours. FIGS. 4F-4G illustrate rates of apoptotic MM under co-culture with MSCs (expressing different levels of Fas-L). Data are presented in FIG. 4G as mean±SD for two parallel experiments. #$P<0.05$ versus the control group (Con.). CFSE, carboxyfluorescein diacetate, succinimidyl ester; DAPI, 4',6-diamidino-2-phenylindole.

FIGS. 5A-5E illustrate the effect of mesenchymal stem cells having highly activated Fas ligand on multiple myeloma model mice. FIG. 5A presents data for five-week survival rates of multiple myeloma (MM) model mice. FIG. 5B shows a comparison of the number (left) and size (right) of cancroid pearls in MM model mice after treatment with mesenchymal stem cells (MSCs) expressing different levels of Fas ligand (Fas-L). In FIG. 5B, data are presented as mean±standard deviation (SD) for three parallel experiments. *$P<0.05$ versus MSC group; #$P<0.05$ versus the control group. FIG. 5C shows representative photographs of typical cancroid pearls at the base of the tail (bar=about 5 mm). FIG. 5D illustrates distribution of cancroid pearl size in the four test groups (n=14). FIG. 5E presents slides showing apoptosis of MM cells in MM model mice. The pearls in each group were triple-stained for 4',6-diamidino-2-phenylindole (blue), Scar-1 (green) and Annexin V/7AAD (red). All groups treated with MSCs had Scar-1-positive cells in the pearls. However, the positive reactions of apoptosis marker in the MSC (gld) group were much lower than those observed in other groups. The MSC(Asp) group had the highest number of reactions among all groups (bar=about 5 μm). Lower panels stained through the terminal deoxynucleotidyl transferase-mediated UTP nick-end labeling (TUNEL) assay. Positive reactions were observed in both MSC and MSC(Asp) groups. ASP, aspirin; Con, control; gld, generalized lymphoproliferative disease.

DETAILED DESCRIPTION OF ILLUSTRATIVE EMBODIMENTS

Figure 1A:
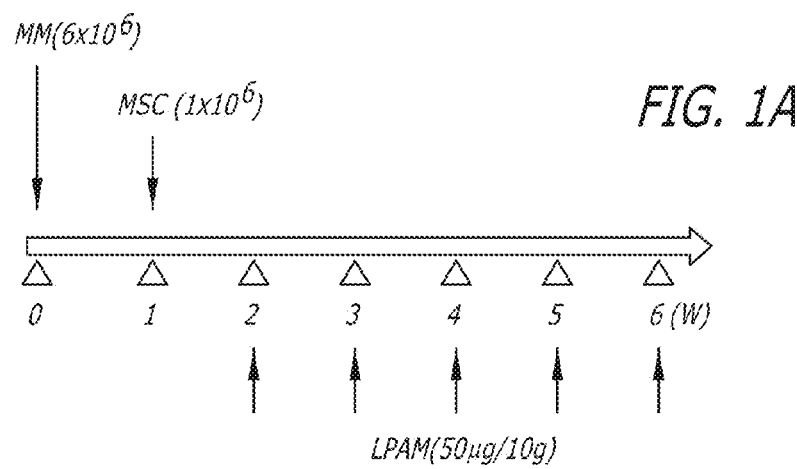

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

Following acronyms were used.
Asp: Aspirin
BD: Bone density
BMMSC: Bone marrow derived mesenchymal stem cells
Con or Cont: Control
Co-cul: Co-culture
ELISA: enzyme-linked immunosorbent assay technique
Fas-L: Fas ligand.
gld: Generalized lymphoproliferative disease.
GMSC: Gingiva derived mesenchymal stem cell.
MSC: Mesenchymal stem cell
IL: Interleukin.
L-PAM: Lymphocyte Peyer's patch adhesion molecules.
MM: Multiple myeloma.
MSC: Mesenchymal stromal cell.
PBS: Phosphate-buffered saline.
RANKL: Receptor activator of nuclear factor κB ligand.
RT-PCT: Reverse transcription polymerase chain reaction.
SD: Standard deviation
TNF: Tumor necrosis factor.
TUNEL: Terminal deoxynucleotidyl transferase-mediated UTP nick-end labeling.
μg: Microgram.
μm: Micrometer.

This disclosure relates in general to a stem cell treatment. This disclosure further relates to a stem cell treatment using a composition comprising stem cells having highly expressed Fas-L. This disclosure further relates to a stem cell treatment of multiple myeloma. This disclosure also relates to a composition comprising stem cells having highly expressed Fas-L. This disclosure also relates to preparation of a composition comprising stem cells having highly expressed Fas-L. This disclosure also relates to preparation of a composition comprising stem cells having highly expressed Fas-L by using aspirin. This disclosure also relates in general to a mesenchymal stem cell (MSC) therapy ("MSC therapy"). This disclosure particularly relates to a therapy by using a composition comprising MSCs having highly expressed Fas Ligand (Fas-L). This disclosure further relates to preparation of a composition comprising MSCs having highly expressed Fas Ligand (Fas-L). This disclosure also relates to a treatment of multiple myeloma (MM) using a composition comprising MSCs having highly expressed Fas-L.

An example of a stem cell treatment was disclosed in a publication by Atsuta et al. "Mesenchymal stem cells inhibit multiple myeloma cells via the Fas/Fas ligand pathway" Stem Cell Research & Therapy, 2013, 4:111. The entire content of this publication is incorporated herein by reference.

The stem cell treatment (or stem cell therapy) includes, but is not limited to, diagnosis, treatment, therapy, cure, healing, mitigation, or prevention of a disease or injury in, and/or cosmetic treatment of a mammal.

The mammal may be a human. The mammal may be a non-human animal. For example, the mammal may be a non-human primate, a horse, a sheep, a cattle, a hog, a dog, a cat, and a goat.

This disclosure relates to a composition. The composition may be a cell culture. The composition may be a drug or a biologic formulation. The composition may be used in the treatment of a disease. An exemplary composition may comprise a stem cell having highly expressed Fas-L. An exemplary composition may comprise an MSC having highly expressed Fas-L.

Stem cells, which are suitable for preparation of the exemplary composition, may be any stem cell of any mammal. For example, the stem cells may be stem cells of a mammal that undergoes the treatment (i.e. autologous stem cell treatment). Or, the stem cells may be stem cells of a mammal other than the mammal that undergoes the treatment (i.e. allogeneic stem cell treatment).

Examples of the stem cells may be embryonic stem cells, fetal stem cells, adult stem cells, amniotic stem cells, cord blood stem cells, induced pluripotent stem cells, or combinations thereof.

An example of the stem cells, that are useful in the preparation of the composition, may comprise a mesenchymal stem cell. Examples of mesenchymal stem cells may comprise bone marrow-derived mesenchymal cells, dental pulp stem cells, stem cells from human exfoliated deciduous teeth, periodontal ligament stem cells, dental follicle stem cells, tooth germ progenitor cells, stem cells from the apical papilla, oral epithelial progenitor/stem cells, gingiva-derived mesenchymal stem cells, periosteum-derived stem cells, salivary gland-derived stem cells, adipose derived mesenchymal stem cells, and combinations thereof. Examples of the stem cells may be cultured mesenchymal stem cells, uncultured gingiva-derived mesenchymal stem cells, dental pulp stem cells, bone-marrow-derived stem cells, and combinations thereof.

One example of the stem cells, that is useful in the preparation of the composition, may comprise a bone marrow derived mesenchymal stem cell (BMMSC). Thus, the composition may comprise a stem cell having highly expressed Fas-L, wherein the stem cell may be the BMMSC.

Another example of the stem cells, that is useful in the preparation of the composition, may comprise a gingiva derived mesenchymal stem cell (GMSC). Thus, the composition may comprise a stem cell having highly expressed Fas-L. The stem cells may be the GMSCs. For isolation of the GMSCs, for example, see Le et al. in a United States patent application publication, entitled "Gingiva Derived Stem Cell and Its Application in Immunomodulation and Reconstruction", Publication No. U.S. 2012/0128636 A1; and Shi et al. in a Patent Cooperation Treaty (PCT) patent application, entitled "A Composition of Mesenchymal Stem Cells", Application No. PCT/US2014/043918. The entire contents of these applications are incorporated herein by reference.

This disclosure also relates to a method of preparation of the composition ("preparation method").

One example of the preparation method may comprise obtaining a tissue, separating the tissue into cells, sorting a stem cell having highly expressed Fas-L, and preparing a composition comprising the stem cells having highly expressed Fas-L.

Another example of the preparation method may comprise obtaining a plurality of tissues, separating these tissues into cells, sorting the stem cells, determining their Fas-L level, and using the stem cells that have higher Fas-L expression level in the preparation of the composition. In this example, the plurality of tissues may comprise obtained from different tissues of a mammal. For example, the first tissue may be a bone marrow tissue and the second tissue may be a gingival tissue.

Yet, in another example, the tissue or the stem cells may be treated to activate or increase the level of Fas-L expression. For example, the tissue or the stem cells may be treated with a salicylate to activate or increase the level of Fas-L expression. This treatment may activate or increase the Fas-L expression level. For example, the tissue or the stem cell may be treated with a salicylate to activate or increase the level of the Fas-L expression. For example, the preparation method may comprise obtaining a tissue, treating the tissue with a salicylate, and preparing a composition comprising the tissue that may comprise the stem cells having highly expressed Fas-L. In one example, the preparation method may comprise obtaining a tissue, separating the tissue into cells, sorting the stem cells, treating the stem cells with a salicylate, and preparing a composition comprising the stem cells having highly expressed Fas-L. In another example, the preparation method may comprise obtaining a tissue, treating the tissue with a salicylate, separating the treated tissue into cells, sorting the stem cells, and preparing a composition comprising the stem cells having highly expressed Fas-L. For the treatment method, an example of salicylate is aspirin.

The aspirin treatment of stem cells are disclosed, for example by Yamaza et al. in "Pharmacologic stem cell based intervention as a new approach to osteoporosis treatment in rodents" PLoS ONE. 2008; 3:e2615; and Chen et al. in "Telomerase governs immunomodulatory properties of mesenchymal stem cells by regulating FAS ligand expression" EMBO Molecular Medicine, 2014, 6(3), 322-334. The entire contents of these publications are incorporated herein by reference.

The aspirin treatment may be carried out at any aspirin level. For example, the stem cells may be treated in a solution comprising aspirin. The solution may comprise aspirin with a concentration varying in the range of 1 µg/ml to 1,000 µg/ml. The aspirin concentration may vary in the range of 5 µg/ml to 200 µg/ml. The aspirin concentration may also vary in the range of 25 µg/ml to 100 µg/ml. The aspirin treatment of stem cells may be carried out for a duration varying in the range of 1 hour to 100 days. The aspirin treatment duration may vary in the range of 1 day to 20 days. The aspirin treatment duration may also vary in the range of 3 days to 10 days.

In one exemplary preparation method, the salicylate may be separated from the MSCs to obtain substantially salicylate-free MSCs. These substantially salicylate-free MSCs may be used in the preparation of the composition. For example, the substantially aspirin-free MSCs may be used in the preparation of the composition.

As disclosed in above examples, the preparation method may comprise obtaining a tissue. The tissue may be any tissue. For example, the tissue may comprise a mammalian tissue. In one example, the tissue may comprise a bone marrow tissue. In another example, the tissue may comprise a gingival tissue. The mammal may be a human. The mammal may be a non-human animal. For example, the mammal may be a non-human primate, a horse, a sheep, a cattle, a hog, a dog, a cat, and a goat. The tissue may comprise a stem cell. The stem cells may be any stem cells. For example, the stem cells may be any stem cells disclosed above.

The tissue may be obtained from a mammal that undergoes the treatment. In this method, the treatment may be an autologous stem cell treatment. The tissue may be obtained from a mammal other than the mammal that undergoes the treatment. In this method, the treatment may be an allogeneic stem cell treatment. Combination of said treatment methods may also be applied. For example, the treatment may comprise an autologous stem cell treatment and an allogeneic stem cell treatment.

The separating the tissue into cells may be done by a mechanical method, a chemical method, or a combination of a mechanical and a chemical method.

Examples of the mechanical method may be mincing, shredding, filtering, and the like. In other examples, the tissue may be separated into cells by using homogenizers, ultrasonicators, ball mills, and the like. A combination of these mechanical methods may also be used to have separated cells.

Examples of the chemical method may be digestion of the tissue by using acids, bases, and enzymes. For example, a collagenase and a dispase may be used to digest the tissue. The collagenase may be collagenase type I. The dispase may be dispase II. A combination of these chemical methods may also be used to have separated cells.

The preparation method may further comprise preparing cell suspensions from the digested tissue by using a mechanical method. An example of such method may be filtering the digested tissue to obtain cell suspensions. The cell suspensions may be single-cell suspensions. For example, single-cell suspensions may be obtained by passing the digested gingival tissue through a 70-μm strainer.

The culturing the separated cells may comprise providing a solid surface, seeding the cells on the solid surface, culturing the seeded cells, and thereby obtaining a culture comprising cells that may be adherent to the solid surface ("adherent cells") and cells that may not be adherent to the solid surface ("non-adherent cells").

The solid surface may be a surface of any solid article. For example, it may be a wall of a vessel. The vessel may be any vessel. For example, the vessel may be a petri dish or a cell-culture dish. The solid article may also be a bead or a particle. The solid article may have any size. For example, it may be a nano-particle.

The cell may be seeded using a solution. The solution may comprise a medium suitable for culturing the mammalian cell. An example of such medium may be α-MEM manufactured by Invitrogen (Carlsbad, Calif.). The solution may further comprise fetal bovine serum (FBS), L-glutamine, 2-mercaptoethanol, penicillin, and streptomycin.

The preparation method may further comprise eliminating from the culture the cells that are not adherent to the solid surface. For example, the culture may be washed by PBS to eliminate from the culture the cells that are not adherent to the solid surface.

The adherent cells may further be cultured, for example, in the same conditions disclosed above.

The preparation method may further comprise dissociating from the solid surface the cells that may be adherent to the solid surface. The adherent cells may be dissociated from the solid surface by using an enzyme. The enzyme, for example, may be trypsin.

The preparation method may further comprises expanding the cultured cells. For example, the expanding the cultured cells may comprise doubling stem cells by repetitively re-seeding them using the preparation methods disclosed above.

As disclosed in above examples, the preparation method may comprise the separating the tissue into cells and sorting the stem cells. Some examples of the separating the tissue into cells and the sorting the stem cells are previously disclosed. For example, for the separating of the gingival tissue into cells, and sorting and isolating the GMSCs, see Le et al. in a United States patent application publication, "Gingiva Derived Stem Cell and Its Application in Immunomodulation and Reconstruction" U.S. 2012/0128636 A1; and Shi et al. in a Patent Cooperation Treaty (PCT) patent application serial number PCT/US14/43918, "A Composition of Mesenchymal Stem Cells". The entire content of these patent applications are incorporated herein by reference.

The preparation method may further comprise culturing the separated cells before the sorting stem cells. The sorting may comprise sorting fluorescein isothiocyanate positive cells as the stem cells.

The preparation method may further comprise determining the Fas-L expression level of the stem cells. The Fas-L expression of the stem cells may be determined by using any suitable technique. For example, the Fas-L expression level of the stem cells may be determined by using techniques such as a reverse transcription polymerase chain reaction technique (RT-PCT), a Western blotting technique, an immunostaining technique, and an enzyme-linked immunosorbent assay technique (ELISA). The Fas-L expression level of the stem cells may quantitatively be determined.

The composition comprising the MSCs having highly expressed Fas-L may be used in the treatment of inflammatory and/or autoimmune diseases. Examples of the inflammatory and/or autoimmune diseases may be graft-versus-host disease (GvHD), diabetes, rheumatoid arthritis (RA), autoimmune encephalomyelitis, systemic lupus erythematosus (SLE), multiple sclerosis (MS), systemic sclerosis, osteoporosis, periodontitis, inflammatory bowel disease (IBD), alimentary tract mucositis induced by chemo- or radiotherapy, and sepsis.

The composition comprising the MSCs having highly expressed Fas-L may also be used in the treatment of multiple myeloma (MM). The composition comprising the MSC having highly expressed Fas-L may be used in the treatment of MM in vivo. The composition comprising the MSC having highly expressed Fas-L may be used in the treatment of MM in vitro.

The composition comprising the MSCs having highly expressed Fas-L may be used for tissue regeneration by local implantation or immune therapies by systemic infusion (via vein).

Other exemplary embodiments of this disclosure are as follows.

EXAMPLE 1

Materials and Methods

Multiple Myeloma Cell Line.

The 5TGM1 MM cell line used in the present study was subcloned from a stroma-independent cell line originally established from parent murine 5 T33 (IgG2bκ) MMs. See, for example, LeBlanc et al. "Proteasome inhibitor PS-341 inhibits human myeloma cell growth in vivo and prolongs survival in a murine model" Cancer Res 2002, 62:4996-5000. The entire content of this publication is incorporated herein by reference. The cell line was grown in long-term suspension culture in Isocove's modified Dulbecco's medium (Invitrogen Co., Carlsbad, Calif., USA) with 10% fetal bovine serum (Summit Biotechnology, Fort Collins, Colo., USA) and antibiotics. In the tracing experiment, MM cells were stained with carboxyfluorescein diacetate, succinimidyl ester (Invitrogen Co.).

Isolation of Bone Marrow Mesenchymal Stem Cells.

Bone marrow cells were flushed from the bone cavity of femurs and tibias of B6 mice (C57BL/6 J) with about 2% heat inactivated fetal bovine serum (Equitech-Bio, Kerrville, Tex., USA) in PBS, and MSCs positive for CD73, CD90, CD105, CD146, CD166, Sca-1 and SSEA-4, but negative for CD11b, CD31, CD34 and CD45, were obtained as previously described by Liu et al. "Mesenchymal stem cell-based tissue regeneration is governed by recipient T lymphocytes via IFN-γ and TNF-α" Nat Med 2011, 17:1594-1601. The entire content of this publication is incorporated herein by reference. The cells with MSC character were cultured with alpha minimum essential medium (Invitrogen) supplemented with about 20% fetal bovine serum and 2 mM L-glutamine (Invitrogen) in a humidified atmosphere of about 95% air and about 5% $CO_2$ at about 37° C. for about 3 days before co-culture. See Oyajobi et al. "Dual effects of macrophage inflammatory protein-1alpha on osteolysis and tumor burden in the murine 5TGM1 model of myeloma bone disease" Blood 2003, 102:311-319. The entire content of this publication is incorporated herein by reference. Additionally, MSCs, which had no Fas-L, were isolated from generalized lymphoproliferative disease (gld) mice for use in comparative experiments. B6 and gld mice in the same background (B6Smn.C3-Faslgld/J) were purchased from the Jackson Laboratory.

5TGM1 Multiple Myeloma Model and MSC Administration.

A 5TGM1 MM model was conducted in weight-matched, 8-week-old to 10-week-old female bg-nu/nu-xid mice from the Jackson Lab (Bar Harbor, Me., USA). The use of animals for research was approved through the Institutional Ethics Committee/Institutional Review Board of the University of Southern California (protocol #10941). The mice were housed in isolator cages, and autoclaved chow and acidified water were provided ad libitum. Disseminated MM was induced through the intravenous inoculation of about $6 \times 10^6$ 5TGM1 cells in about 200 μl PBS in bg-nu/nu-xid mice through the tail vein (about $6 \times 10^6$/10 g body weight). After tumor cell inoculation, multiple MM model mice were randomized to receive the injection of either MSCs (once, about $1 \times 10^6$ MSCs/10 g body weight) via the tail vein (MSC group) or lymphocyte Peyer's patch adhesion molecules (L-PAM; weekly, about 50 μg/10 g body weight) in the abdominal cavity (L-PAM group), as shown in FIG. 1A. See Akiyama et al. "Mesenchymal-stem-cell-induced immunoregulation involves FAS-ligand/FAS-mediated T cell apoptosis" Cell Stem Cell 2012, 10:544-555. The entire content of this publication is incorporated herein by reference. L-Phenylalanine mustard, or L-PAM, otherwise known as melphalan, is used as the standard treatment in older MM patients. See Musto P. et al. "Melphalan: old and new uses of a still master drug for multiple myeloma" Expert Opin Investig Drugs 2007, 16:1467-1487. The entire content of this publication is incorporated herein by reference. MM model mice with no treatment served as the positive control (MM group). Original nude mice with no treatment served as the negative control (Control group). The 6-week survival rates of the mice in different groups were compared. After about 4 weeks of feeding, the cancroid pearls in the neck, tail root and abdominal cavity of the mice in different groups were identified for analysis. For the analysis of the cancroid pearls, see Oyajobi et al. "Dual effects of macrophage inflammatory protein-1 alpha on osteolysis and tumor burden in the murine 5TGM1 model of myeloma bone disease" Blood 2003, 102:311-319. The entire content of this publication is incorporated herein by reference. For tissue preparation and immunohistochemistry, the animals were housed and provided water and a powdered diet until the time of humane sacrifice.

Microcomputed Tomography Analysis.

The cross-sectional volumetric bone mineral density was measured in right femur diaphysis of the mice in each group after about 4 weeks of feeding (for each group, n=6). High-resolution whole-body radiographs of ketamine anesthetized mice were obtained with the Inveon microcomputed tomography system (Siemens AG, Bensheim, Germany). Using two-dimensional images, a region of interest in secondary spongiosa was manually drawn near the endocortical surface, and cancellous bone morphometric parameters including the bone volume relative to the tissue volume (percentage) and the trabecular thickness (millimeters) were assessed. A trained observer blinded to the composition of the different groups and treatments received analyzed the number and surface area of radiolucent lesions.

Tissue Preparation and Immunohistochemistry.

Tissue preparation was performed following the publication by Zhang et al. "Mesenchymal stem cells derived from human gingiva are capable of immunomodulatory functions and ameliorate inflammation-related tissue destruction in experimental colitis" J. Immunol. 2009, 183:7787-7798. The entire content of this publication is incorporated herein by reference. The mice were sacrificed after about 4 weeks of feeding. The samples were immersed in about 4% paraformaldehyde for about 24 hours and embedded in about 20% sucrose overnight at about 4° C. The samples were immersed in O.C.T. compound (Sakura, Tokyo, Japan) for about 2 hours at about 4° C. and cut into about 6 μm thick bucco-palatal sections using a cryostat at about −20° C. For immunofluorescence staining, the sections were blocked for about 30 minutes with about 10% normal goat serum and incubated overnight with fluorescein isothiocyanate-conjugated polyclonal rabbit Sca-1 IgG (1:100; Vector Laboratories, Burlingame, Calif., USA), 7AAD and Annexin V (Apoptosis Detection Kit; BD Biosciences, Franklin Lakes, N.J., USA) at about 4° C. The other sections were stained with hematoxylin and eosin and photographed using a light microscope. In addition, for terminal deoxynucleotidyl transferase-mediated UTP nick-end labeling (TUNEL), an apoptosis detection kit (Millipore Co., Billerica, Mass., USA) was used in accordance with the manufacturer's instructions.

Cell Culture Conditions.

To determinate the in vitro cellular effects of MSCs on MM and 5TGM1 MM cells were co-cultured with MSCs directly or under Transwell® culture conditions. For direct co-culture, MM cells were plated at about $5 \times 10^5$/ml with or without about $5 \times 10^5$/ml MSCs for about 0 hour, about 6 hours, about 12 hours, or about 24 hours. For in-direct co-culture, Transwell® culture was used. Briefly, the upper chamber (about 0.5 ml culture medium) contained $0.5 \times 10^5$ MSCs, and the bottom chamber (about 1.5 ml medium) contained either the same number or 5 to 10 times that of MM cells. The Transwell® culture without MSCs in the upper chamber served as the control. In the conditioned culture medium, $0.5 \times 10^5$ MSCs were cultured for about 3 days. The supernatant was harvested, added to the MM cultures, and then cultured for about 0 hour, 6 hours, about 12 hours, or about 24 hours.

Flow Cytometric Analysis.

After the MM cells were co-cultured with MSCs for about 0 hour, about 6 hours, about 12 hours, and about 24 hours under Transwell® culture conditions, the cells were harvested, washed in PBS and incubated with Annexin-V-fluorescein isothiocyanate and 7AADPerCP for about 15 minutes at room temperature in the dark. Apoptosis was analyzed on a BD FACSCalibur™ flow cytometer (BD Biosciences, San Jose, Calif., USA), as disclosed by Sun L. Y. "Abnormal surface markers expression on bone marrow CD34+ cells and correlation with disease activity in patients with systemic lupus erythematosus" Clin Rheumatol 2007, 26:2073-2079. The entire content of this publication is incorporated herein by reference.

Western Blotting.

Total cell lysates for western blots were prepared after lysing cell pellets in radioimmunoprecipitation assay buffer. The lysates were separated through about 7.5% SDS-PAGE, transferred to Immobilon™-P nitrocellulose membranes (Millipore, Inc.) and immunoblotted with Fas (about 1:100) or Fas-L (about 1:100) antibodies at about 4° C. overnight. The membranes were subsequently incubated with horseradish peroxidaseconjugated anti-rabbit IgG (about 1:10,000; Santa Cruz Biosciences, Santa Cruz, Calif., USA) for about 1 hour, followed by enhancement with a SuperSignal® West Pico Chemiluminescent Substrate (Thermo, Rockford, Ill., USA). The bands were detected on BIOMAX MR film (Kodak, Rochester, N.Y., USA). Each membrane was also stripped using a stripping buffer (Thermo) and reprobed with anti-β-actin antibody to quantify the amount of loaded protein.

Immunofluorescence Staining for Multiple Myeloma Cells or MSCs.

MM cells and MSCs co-cultured on dishes were fixed in about 4% formaldehyde for about 10 minutes. For fluorescence staining, the samples were treated in about 0.5% (VN) Triton X-100 (Novocastra Laboratories Ltd, Newcastle, UK) for about 3 minutes and incubated with Annexin V/7AAD. The other cells were blocked with about 10% normal goat serum for about 30 minutes at about 37° C. and incubated overnight at about 4° C. with anti-Fas antibodies (about 1:100; Chemicon International Inc. Temecula, Calif., USA) or anti-Fas-L antibodies (about 1:100; Chemicon International Inc.). The samples were incubated with tetramethylrhodamine isothiocynate-conjugated or fluorescein isothiocyanate-conjugated secondary antibodies for about 2 hours at about 37° C. Imaging was performed using an Axiotech Microscope (Carl Zeiss Co. Ltd, Göttingen, Germany).

Statistical Analysis.

Data are expressed as mean±standard deviation for two to four parallel experiments separately repeated. One-way analysis of variance and Fisher's least-significant difference tests were performed. $P<0.05$ was considered statistically significant. The experiments were performed in triplicate and repeated twice or more to verify the results.

EXAMPLE 2

Effects of MSC Infusion on Multiple Myeloma

Figure 1B:
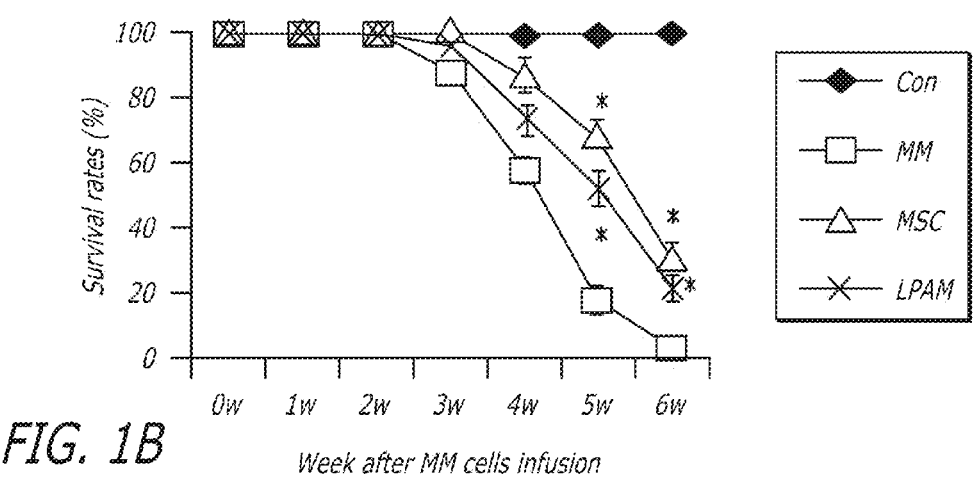

The 6-week survival rates of mice were investigated in this example (for each mice group, n=14). The effect of MSC administration on the 6-week survival rates of MM model mice is shown in FIG. 1B. The survival rate of MM model mice, without any treatment by MSC or L-PAM administration ("MM group"), dramatically decreased until all mice died after about 6 weeks of feeding. MM model mice with MSC ("MSC group") or L-PAM ("L-PAM group") administration had the similar survival rate during the 6-week observation period ($P>0.05$). Although the survival rate of mice in the MSC group or the L-PAM group was lower than that in the Control group (original nude mice without MM cell injection) ($P<0.05$), the administration of either MSCs or L-PAM achieved prolonged survival compared with the MM group ($P<0.05$). No animal in the negative control group died (the original nude mice that did not receive any treatment) after about 6 weeks of feeding.

Figure 1C:
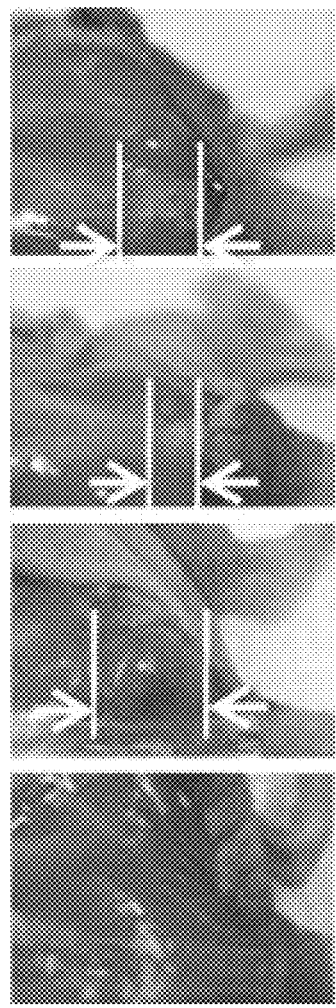
Figure 1D:
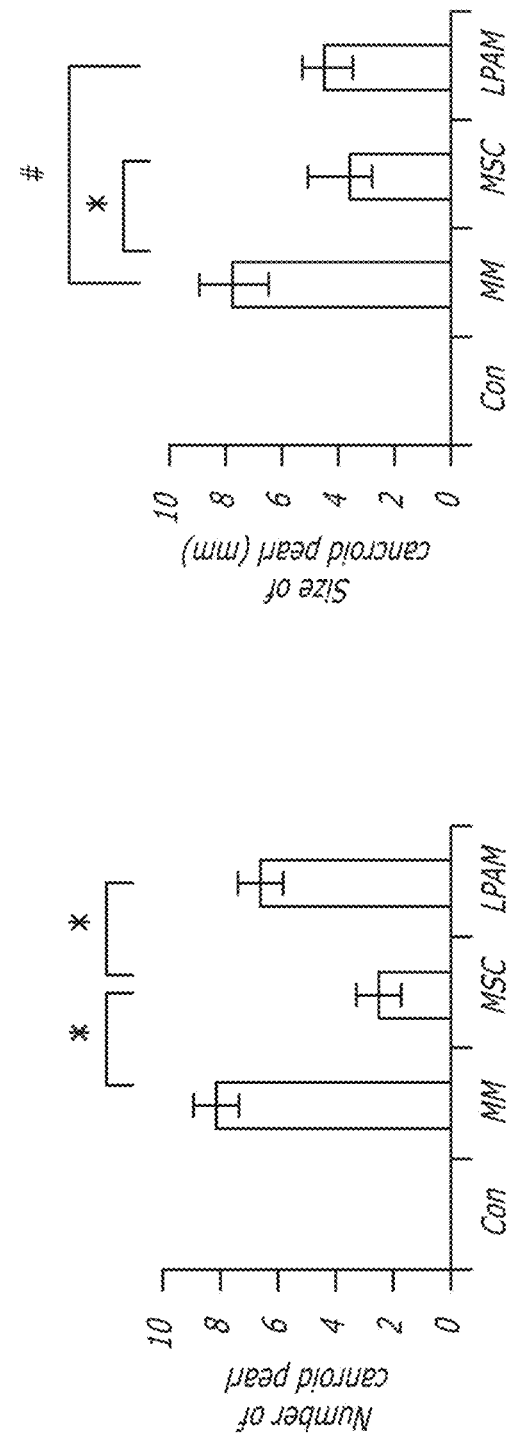

The number and size of cancroid pearls were compared among the four groups (for each group, n=14) after about 4 weeks of feeding, as shown in FIGS. 1C-1D. No cancroid pearls were identified in the negative control group ("Control group"), but significant differences in the number and size of the pearls were observed between the MSC group and the MM group ($P<0.05$). Although the number of pearls showed no significant difference, the size of the pearls in the L-PAM group was smaller compared with the MM group ($P<0.05$). These data indicated that the MSC administration inhibited both the number and the size of cancroid pearls in the MM model mice.

Figure 1E:
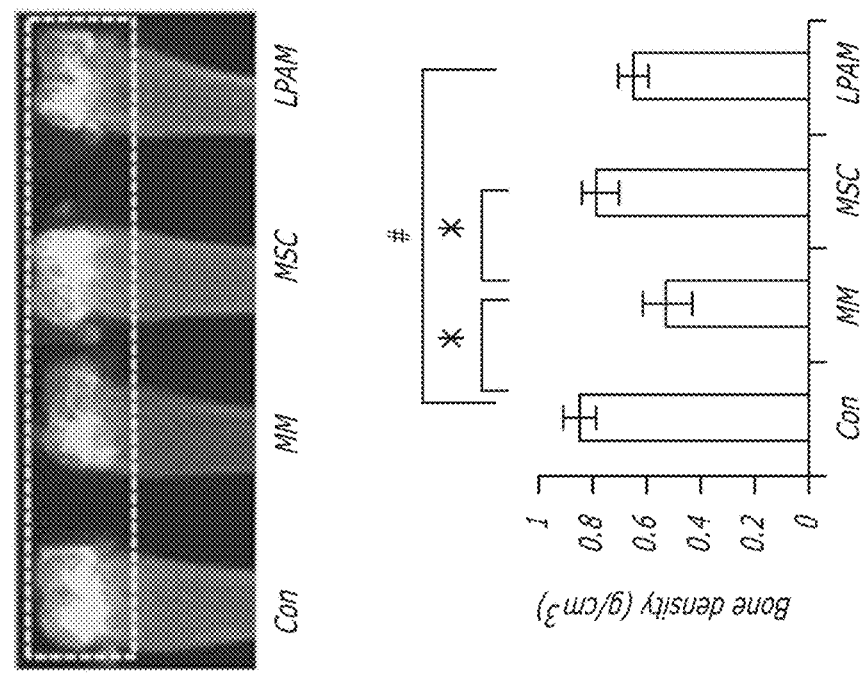
Figure 1F:
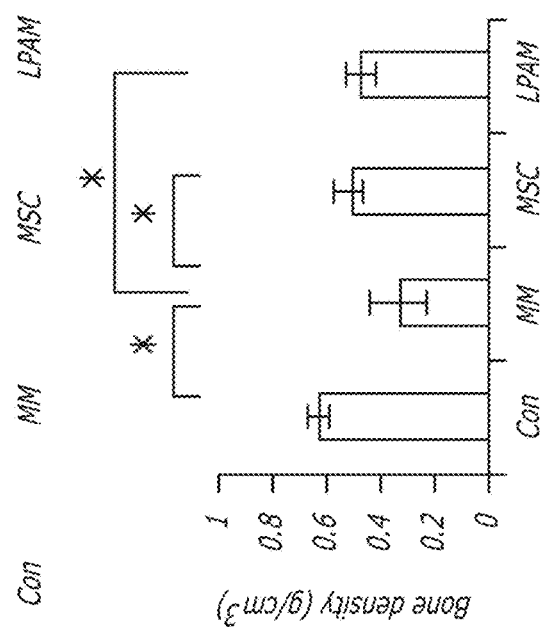

Furthermore, bone resorption in the lumbus and collum femoris of mice in different groups was examined and statistically analyzed through microcomputed tomography after about 4 weeks of feeding (for each group, n=3), as shown in FIGS. 1E-1F. The bone density (BD) in both the lumbus and collum femoris of animals in the MM group was much lower than those of the MSC group, the L-PAM group, and the Control group ($P<0.05$). Although lower than the Control group ($P<0.05$), no significant differences were observed between the MSC group and the L-PAM group ($P>0.05$).

In addition, MM cell metastasis was determined and quantified in the lungs and kidneys of the MM model mice after about 4 weeks of feeding (for each group, n=5), as shown in FIGS. 1G-1H.

The rate of metastasis in the lung tissue obtained from mice in the MSC group was much lower compared with either the MM group or the L-PAM group ($P<0.05$). As for the metastasis rate in the kidney tissue, no significant difference was observed among the MM group, the MSC group, and the L-PAM group ($P<0.05$).

EXAMPLE 3

Effects of MSCs on Multiple Myeloma Cells Under Co-Culture Conditions

Figure 2A:
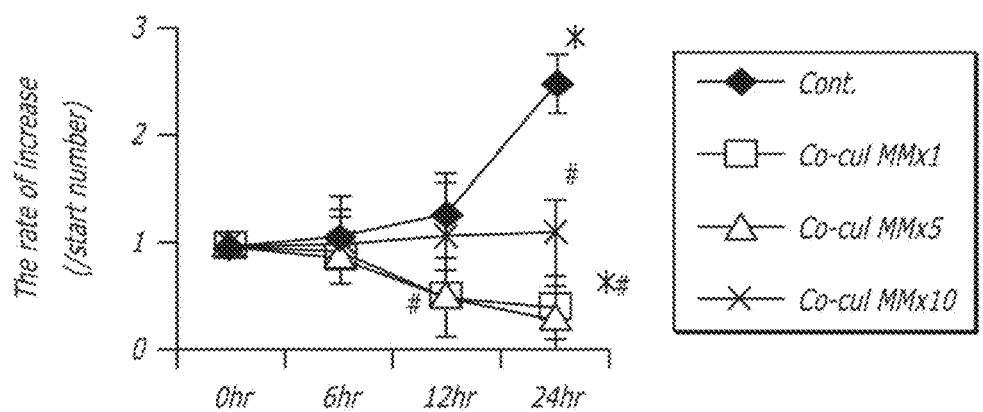
FIGS. 2A-F illustrate the relationship between multiple myeloma cells and mesenchymal stem cells under co-culture conditions.

First, three testing co-culture groups were designed, where the number of MM cells was equal to or five to 10 times greater than that of MSCs. MM cells without MSC co-culture served as the control. In the control group, the MM cell number increased 2.5-fold over the initial cell number at about 24 hours after co-culture. When the initial number of MM cells was equal to or five times greater than that of MSCs, the inhibitory effect of MSCs on MM cell increase was apparent. However, no significant MM cell increase was observed when the number of MM cells was about 10 times the number of MSCs, as shown in FIG. 2A.

Figure 2B:
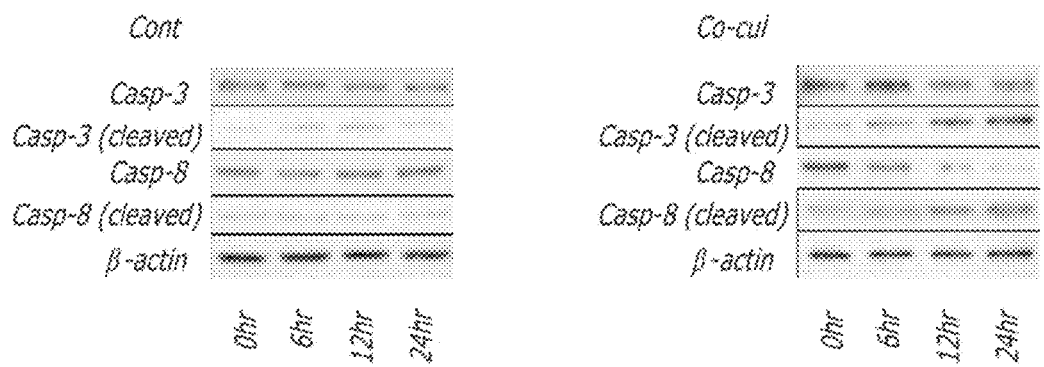
Figure 2C:
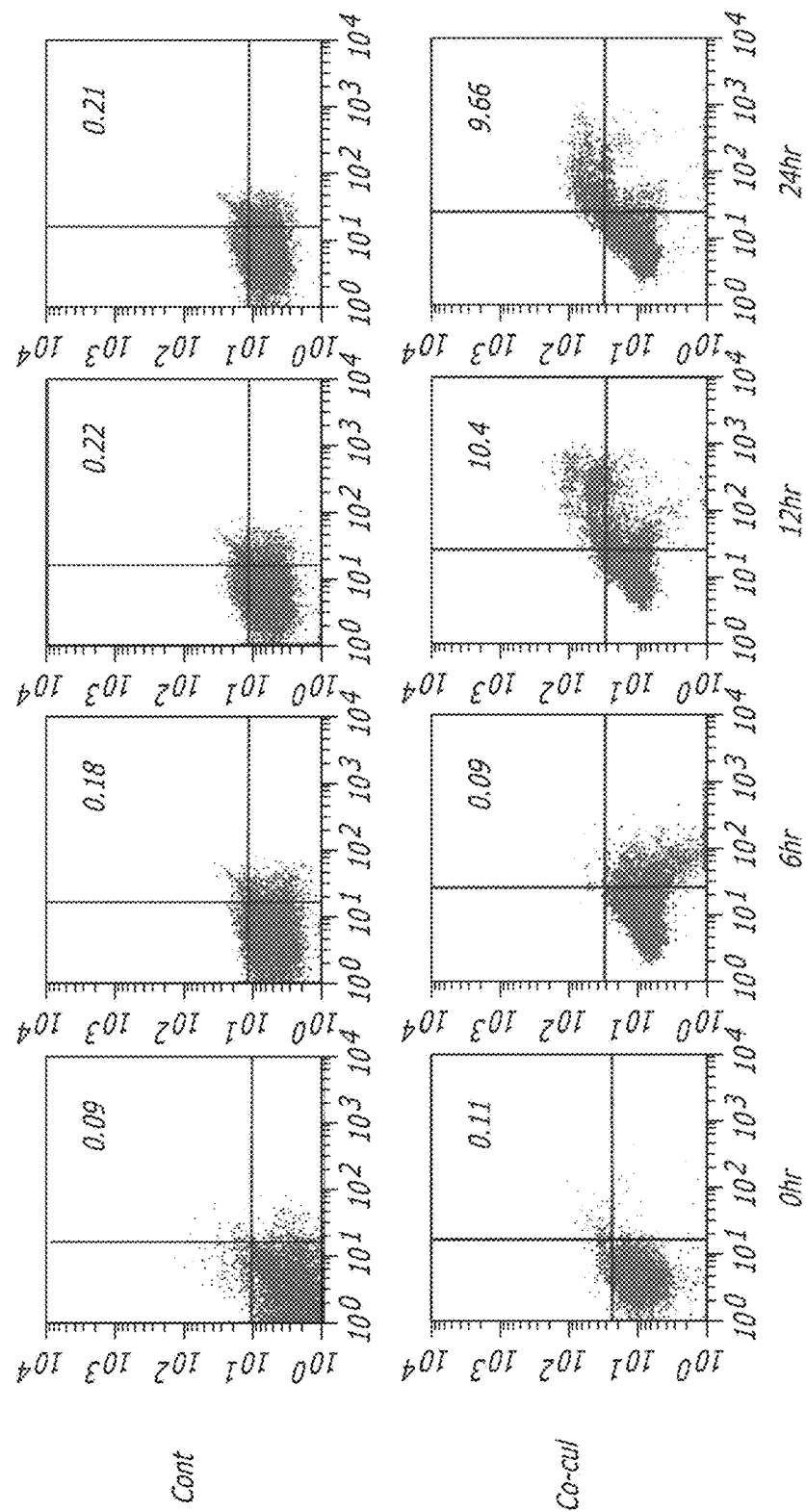
Figure 2D:
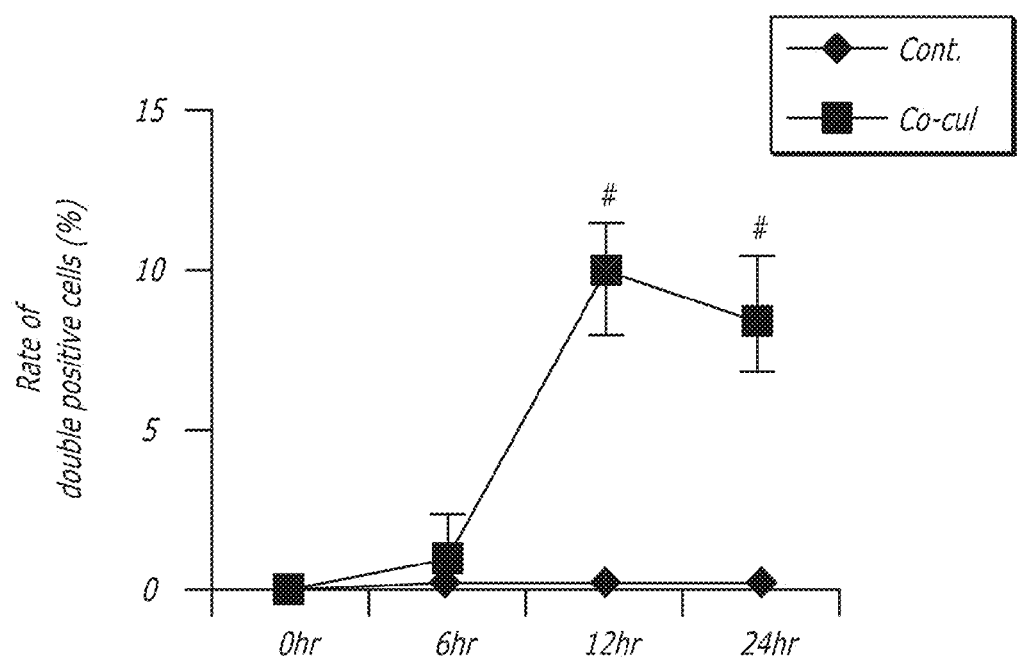
Figure 2E:
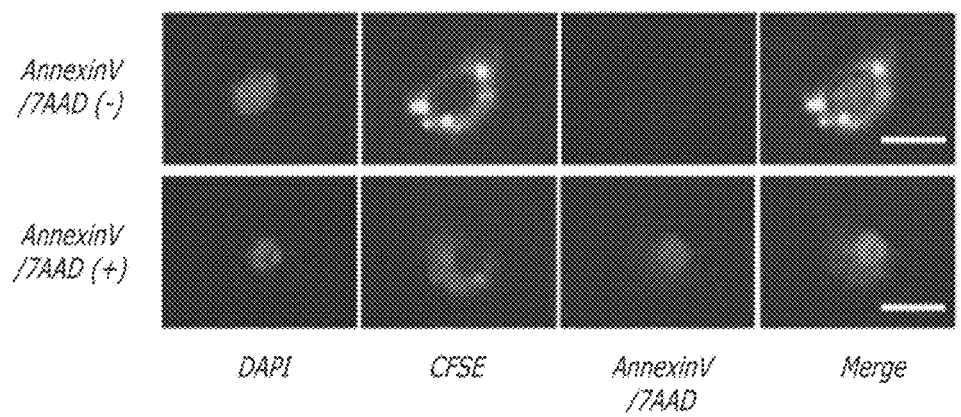
Figure 2F:
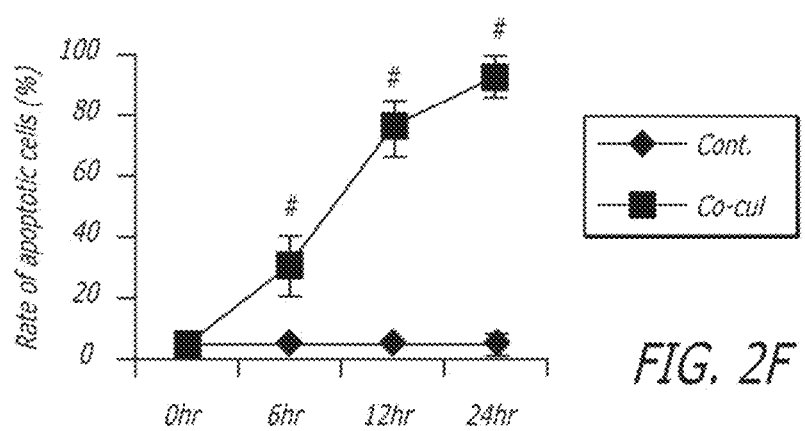

To determine whether the reduction was induced through MM cell apoptosis, caspase-3 and caspase-8 expression in MMs was determined through western blotting. The increased expression of cleaved caspase-3 and caspase-8 was observed in most MM cells after about 12 hours of co-culture, as shown in FIG. 2B. The cleaved caspase-3 and caspase-8 expression in MM cells without co-culture with MSCs was fixed, while the expression of cleaved caspase-3 and caspase-8 in MM cells co-cultured with MSCs was slightly increased. Furthermore, the apoptotic rate of MM cells was examined using fluorescence-activated cell sorting and Annexin V and 7AAD immunofluorescence. It was observed that the apoptotic rate of MM cells, determined and quantified through fluorescence-activated cell sorting analysis, was dramatically changed at about 12 hours after co-culture with MSCs ($P<0.05$), as shown in FIGS. 2C-2D. In the case of immunofluorescence, the number of positive apoptotic markers in MM cells significantly increased after about 6 hours of co-culture (P<0.05), as shown in FIGS. 2E-2F.

EXAMPLE 4

Influence of Fas/Fas Ligand Pathway on Multiple Myeloma Cell Apoptosis

Figure 3A:
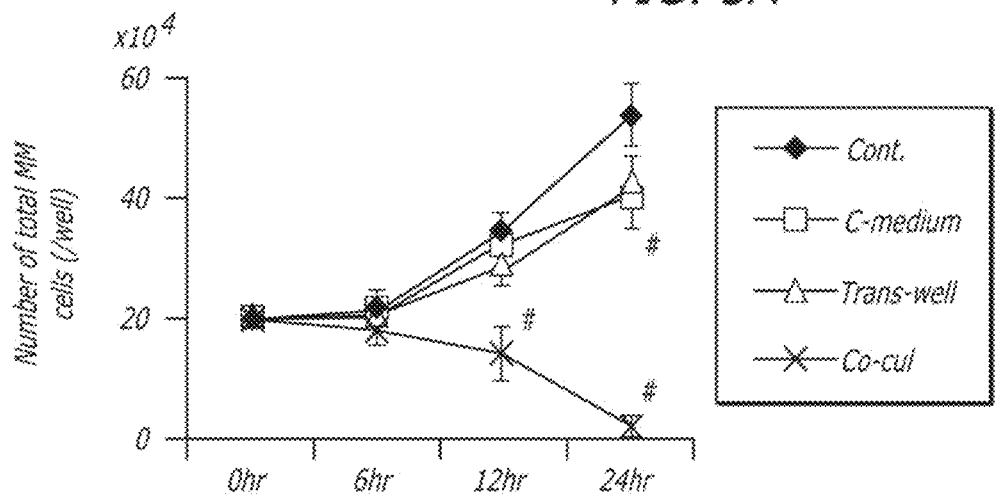
FIGS. 3A-3F depict Fas and Fas ligand analysis in multiple myeloma cells and mesenchymal stem cells under co-culture.
Figure 3B:
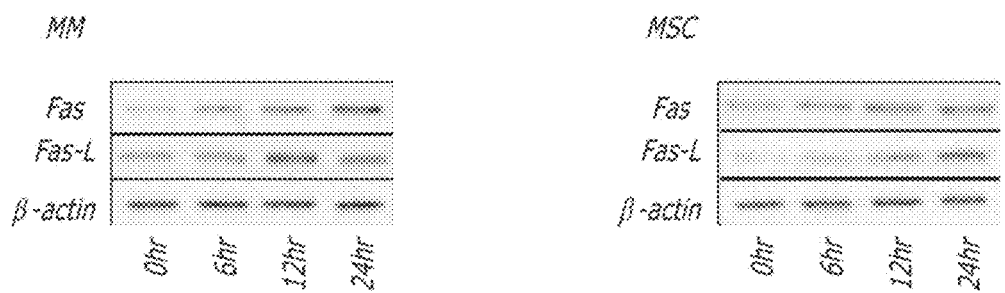
Figure 3C:
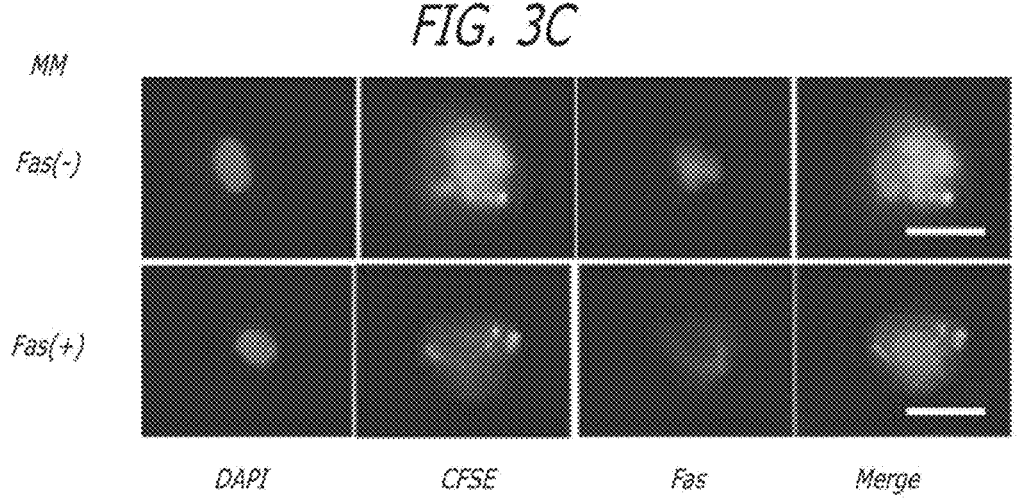
Figure 3D:
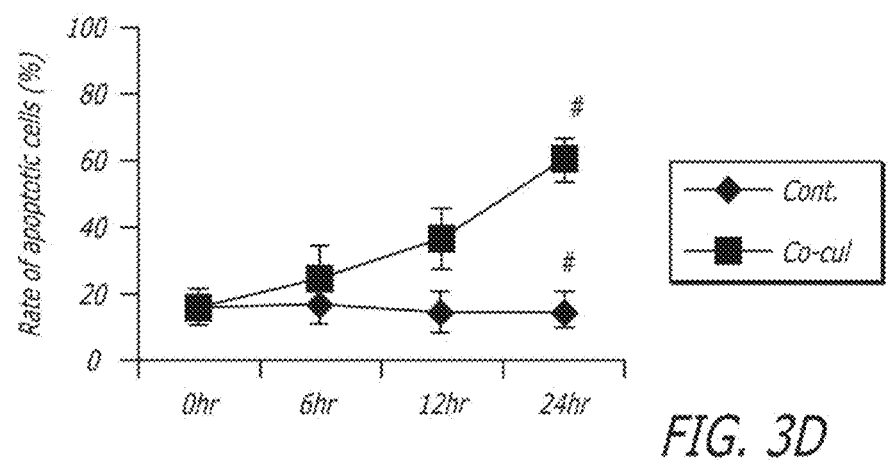
Figure 3E:
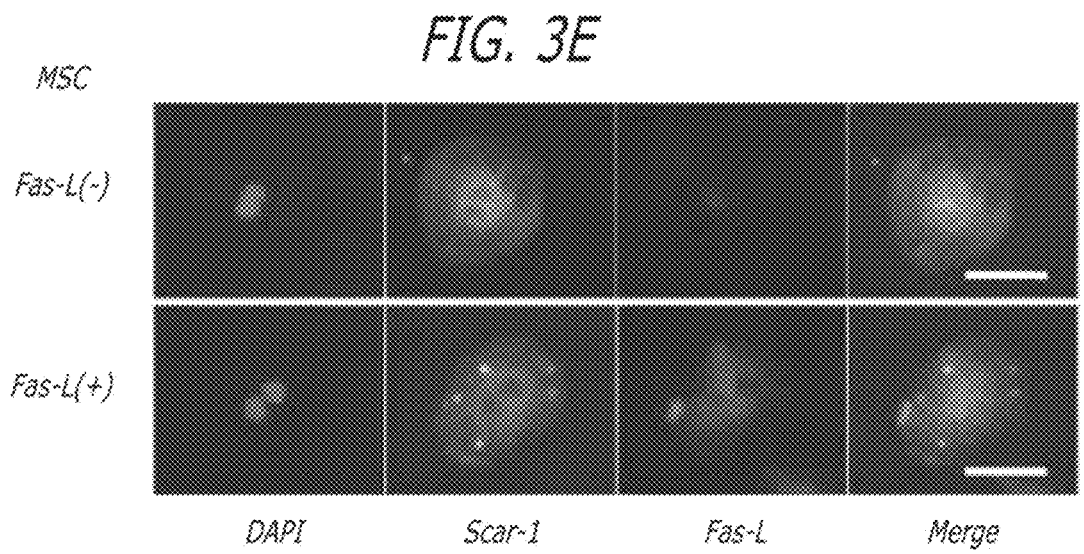
Figure 3F:
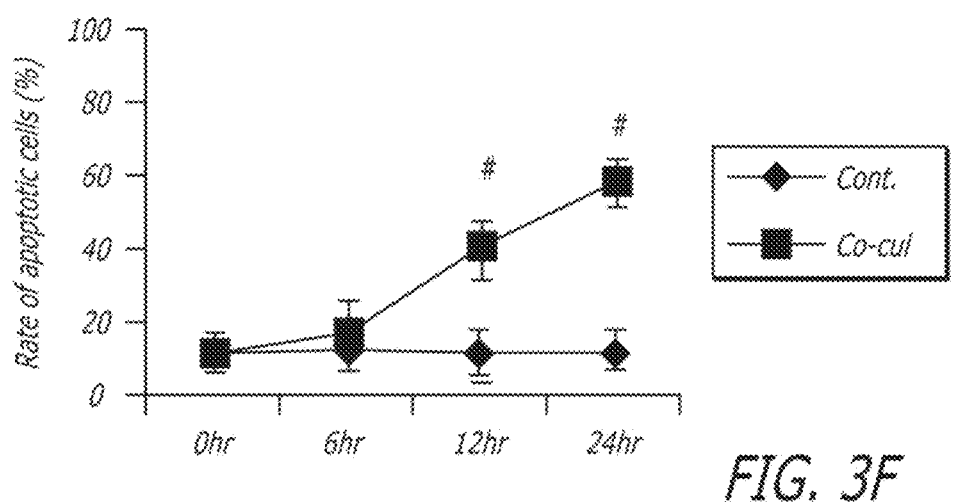

Next, we investigated the different conditions of co-culture with MSCs to confirm the necessity of direct contact between the MSCs and the MM cells for the induction of MM cell apoptosis. Only the direct co-culture group, which shows direct contact between MM cells and MSCs, exhibited a strong inhibitory effect on MM cell growth (P<0.05), as shown in FIG. 3A. In addition, the expression of Fas in MM cells and Fas-L in MSCs, determined through western blotting, increased at about 12 hours and about 24 hours (P<0.05), as shown in FIG. 3B. The data for immunofluorescence staining showed results similar to those of the western blot analysis, as shown in FIGS. 3C-3D.

Figure 4A:
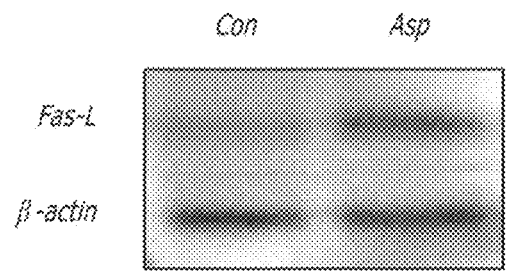
FIGS. 4A-4G illustrate effects of Fas ligand levels in mesenchymal stem cells on multiple myeloma cells under co-culture.
Figure 4B:
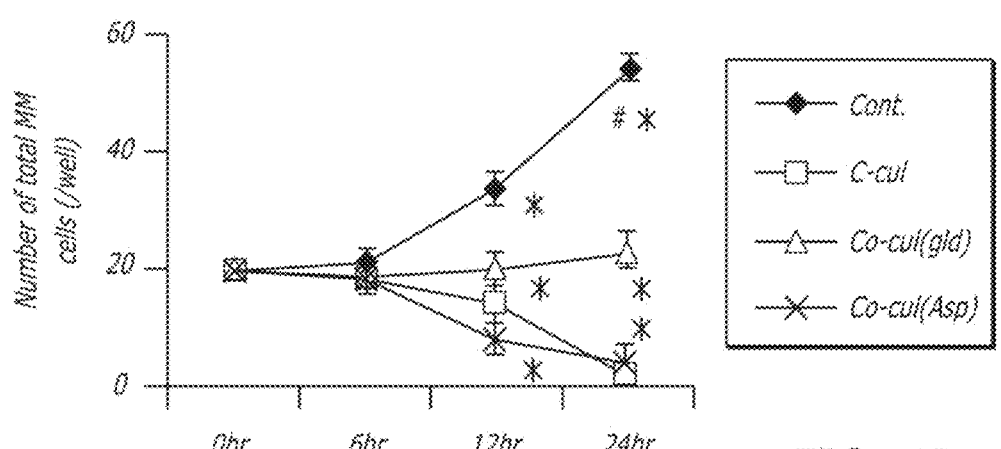
Figure 4C:
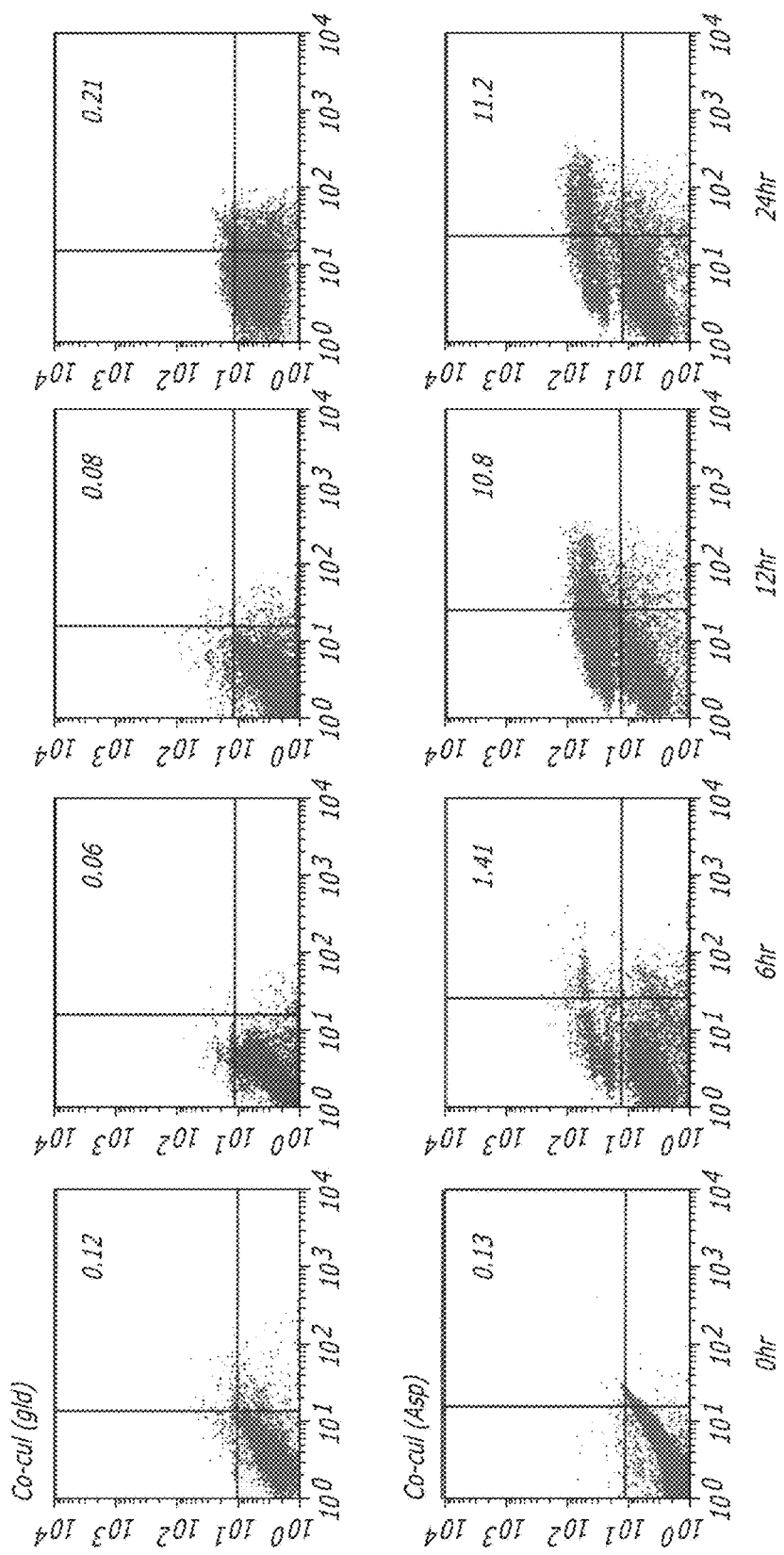
Figure 4D:
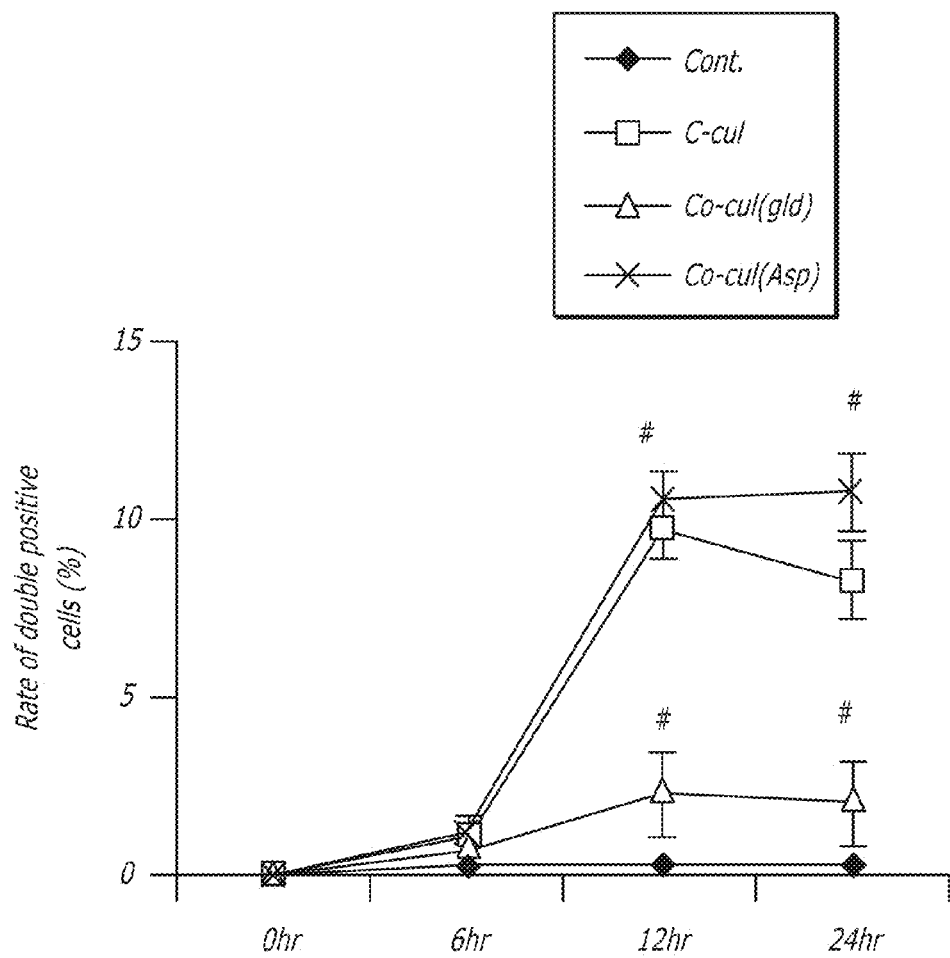
Figure 4E:
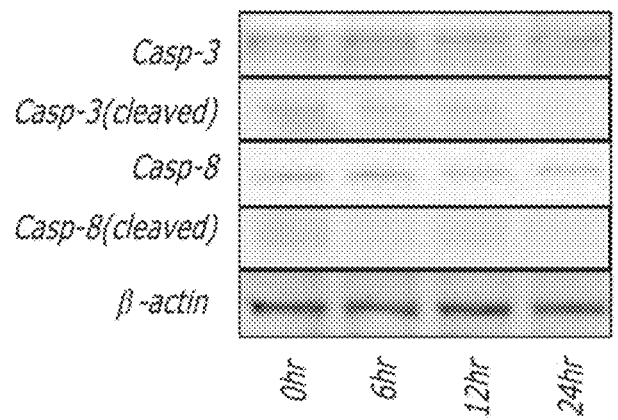
Figure 4E:
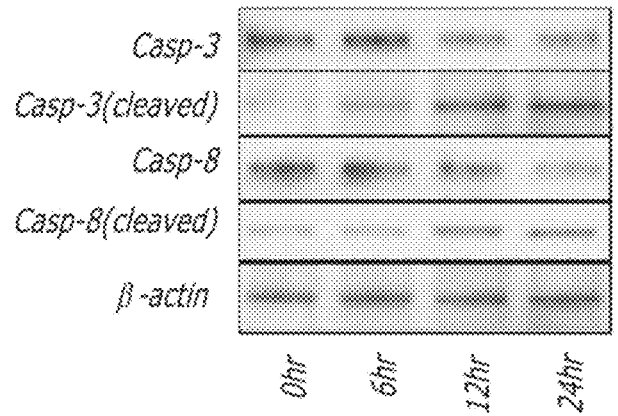
Figure 4F:
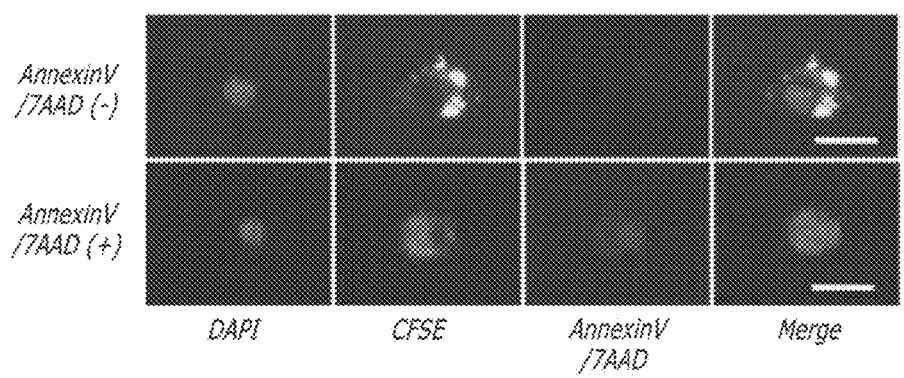
Figure 4G:
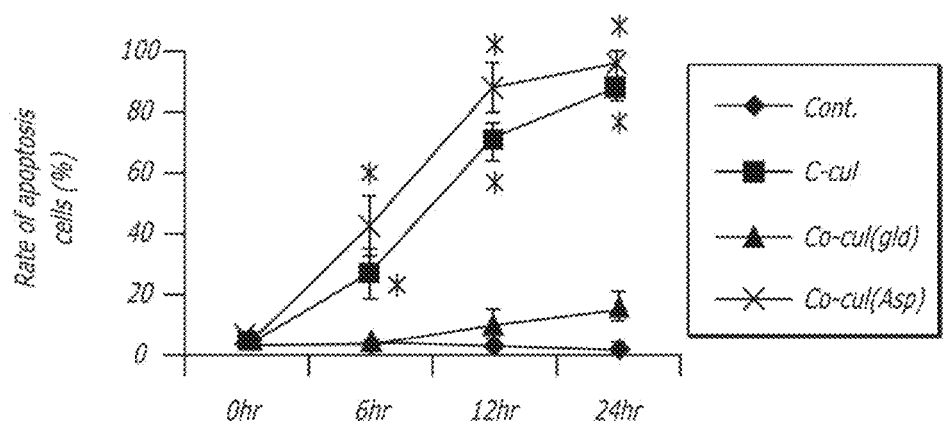

MSCs from gld mice, which had no Fas-L, and aspirin treated MSCs, which had high Fas-L, were used to confirm that the enhancement of Fas-L in MSCs increased the apoptosis of MM cells. Aspirin treatment showed the enhanced expression of Fas-L in MSCs, as shown in FIG. 4A. A reduction in the number of MM cells co-cultured with aspirin-treated MSCs was less than that in the normal co-cultured group (co-cultured with normal MSCs) at about 12 hours (P<0.05), as shown in FIG. 4B. However, co-culture with the MSCs obtained from gld mice had little influence on MM cell growth. Furthermore, the expression of caspase-3 and caspase-8 in MM cells co-cultured with aspirin-treated MSCs was significantly increased after about 12 hours. Under these conditions, the protein expression of cleaved caspase-3 and caspase-8 was reduced after about 12 hours. In the case of the gld group, the expression of these proteins remained unchanged, as shown in FIGS. 4C-4D. The rate of apoptotic cell death was further investigated using fluorescence-activated cell sorting, as shown in FIG. 4E, and immunofluorescence with Annexin V/7AAD, as shown in FIGS. 4F-4G. Aspirin-treated MSCs showed a greater effect on MM cells than normal MSCs (control group) (P<0.05), and MSCs obtained from gld mice showed effects similar to those of normal MSCs.

This example further demonstrated that the treatment of MSCs with a salicylate activated or increased level of Fas-L expression.

EXAMPLE 5

Figure 5A:
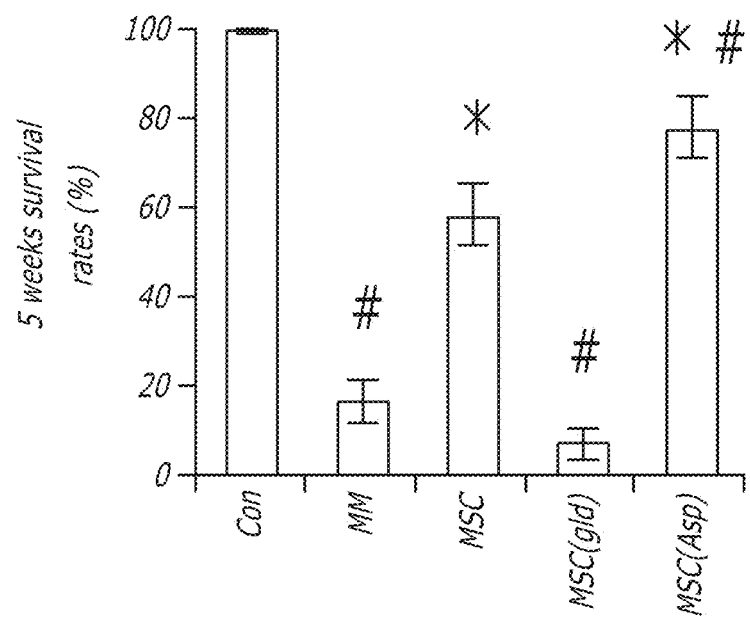
Figure 5B:
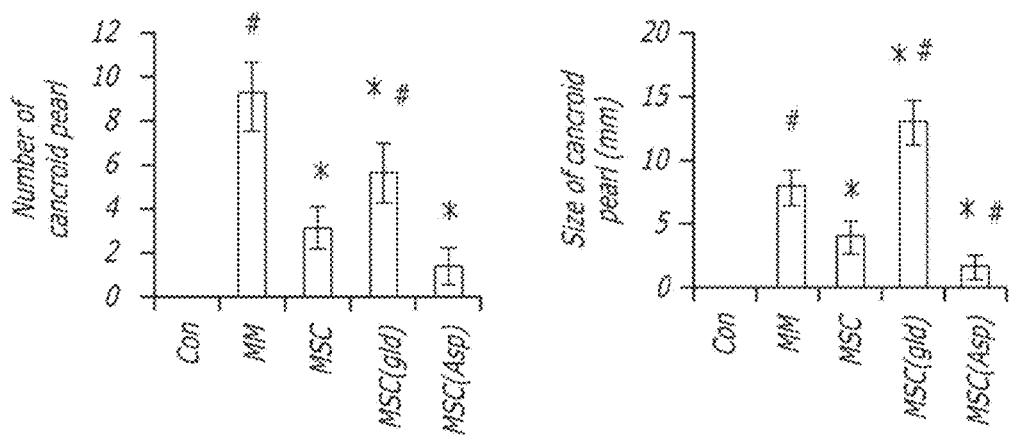
Figure 5C:
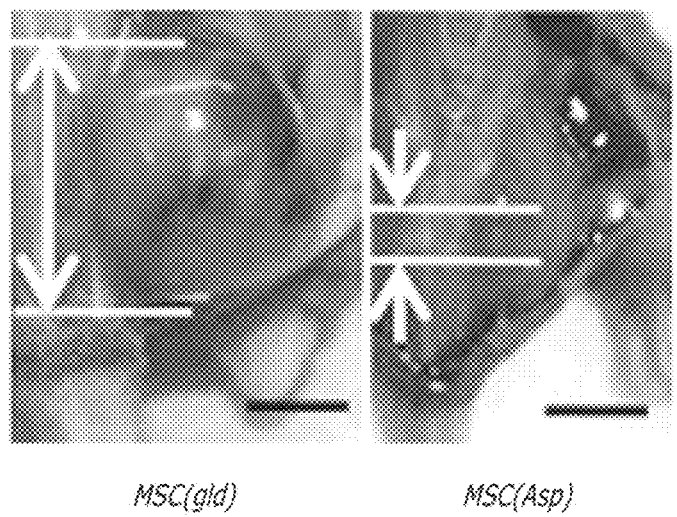
Figure 5E:
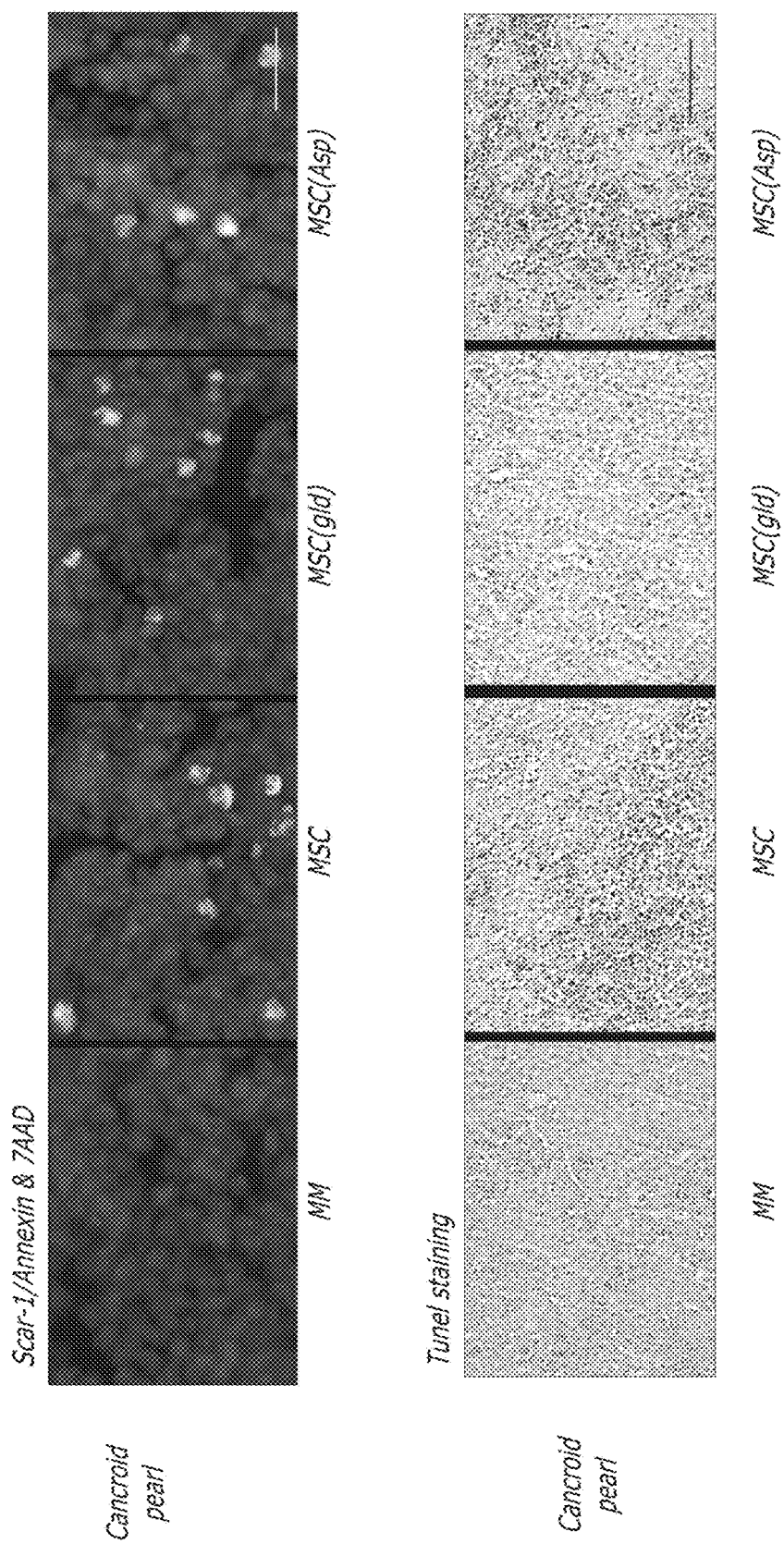

Effects of MSCs Having Highly Expressed Fas Ligand on the Multiple Myeloma Model Mice The MSCs obtained from normal, gld or aspirin-treated mice were used to examine the 5-week survival rates of the MM model mice. The survival rate in the MM model mice treated with aspirin was much higher compared with normal MSC-treated mice (P<0.05). The MSCs obtained from the gld mice showed a reduced survival rate, as shown in FIG. 5A. Furthermore, the number and the size of cancroid pearls were compared among all groups, and both the number and size in the aspirin treated group were lower compared with the normal group. However, the gld treated group showed a significantly larger cancroid pearl size compared with the MM model mice without MSC treatment (MM group), although the number of pearls in the MSC gld treated group was less than that in the MM group, as shown in FIGS. 5B-5C. The distribution of cancroid pearl size in the MM model mice in each group was shown in FIG. 5D. Moreover, the presence of MSCs and the apoptosis of MM cells in the pearls of the MM model mice were observed through immunofluorescence and TUNEL staining. The presence of MSCs was positive in all MSC injection groups, as shown in FIG. 5E.

As shown in above examples, treatment of MSCs having highly expressed Fas ligand (Fas-L$^{high}$ MSCs) indicated remarkable inhibitory effects on MM indenization in terms of extending the mouse survival rate and inhibiting tumor growth, bone resorption in the lumbus and collum femoris, and MM cell metastasis in the lungs and kidneys. That is, the levels of Fas-L expression in MSCs may determine, at least in part, the effect of MSCs on cancer growth.

Above experimental results also indicated that certain phenotypes of MSCs may exhibit inhibitory effects on MM cells, such that the anti-myeloma activity of MSCs can be harnessed or enhanced, for example, via gene-modified approaches.

Experimental results disclosed in above examples further indicated that MSCs may counterattack MM cells using the same mechanism as observed in other cancer cells; namely, Fas-mediated apoptosis. Fas and Fas-L are coexpressed on primary MSCs that might kill co-cultured MM cells. MM cells might thus be susceptible to the induction of apoptosis through MSCs.

That is, MSCs may act directly on MM cells, inhibiting their proliferation. MSC-induced apoptosis in MM cells is evidenced by an increase in the Annexin/7AAD-positive cell population. Most of this effect can be attributed to the Fas/Fas-L pathway.

The activation of both caspase-3 and caspase-8 was observed, suggesting that two main pathways of procaspase activation—the intrinsic mitochondrial pathway and the extrinsic death receptor pathway—may both be involved in MSC-induced apoptosis of MM. Having determined the effects of MSCs activated through aspirin (having highly activated Fas-L) in the MM model mice, these MSCs resulted in a more effective clinical outcome compared with MSCs from the gld mice. The MSCs having high Fas-L expression would be extremely effective in inhibiting MM growth and metastasis. These experimental results disclosed in above examples indicated that infused MSCs moved immediately to the tumor site. However, the positive TUNEL reactions within MSCs from the gld mice were much lower than the others, suggesting that MSCs without Fas-L may have no capacity to kill MM cells.

Fas-L may be expressed on MSCs to induce MM cell apoptosis under co-culture conditions. Furthermore, Fas-L activated through aspirin may effectively inhibit the growth and metastasis of MMs in vitro and in vivo. The additive or synergistic anti-MM activity of MSCs having highly activated Fas-L, measured on the basis of cell growth, apoptosis, and modest survival improvement of MM-bearing mice, indicating that the levels of Fas-L expression in MSCs may determine, at least partially, the effect of MSCs on cancer growth.

Any combination of inventive features disclosed above may be possible and thereby within scope of this disclosure. For example, a method of preparing a composition suitable for a stem cell treatment of a mammal, wherein the preparation method may comprise obtaining a tissue comprising a stem cell, separating the tissue into cells, sorting the stem cell, treating the stem cell, and preparing a composition comprising the treated stem cell having highly expressed Fas-L. In another example, a method of preparing a composition suitable for a stem cell treatment of a mammal, wherein the preparation method may comprise obtaining a tissue comprising a stem cell, treating the tissue, separating the treated tissue into cells, sorting the stem cell, and preparing a composition comprising the treated stem cell having highly expressed Fas-L. In these examples, the tissue or a stem cell may be treated by using a salicylate. An example of a salicylate may be aspirin. In these examples, the using a salicylate may comprise preparing a solution comprising a salicylate at a predetermined salicylate concentration for a predetermined salicylate treatment duration. The predetermined salicylate concentration may vary in the range of 1 µg/ml to 1,000 µg/ml, or in the range of 5 µg/ml to 200 µg/ml, or in the range of 25 µg/ml to 100 µg/ml. The predetermined salicylate treatment duration may vary in the range of 1 hour to 100 days, or in the range of 1 day to 20 days, or in the range of 3 days to 10 days. In these examples, an example of a salicylate may be aspirin. In these examples, the tissue may comprise a bone marrow tissue, a gingival tissue, or combinations thereof. In these examples, the stem cell may comprise an MSC. Examples of MSC may be bone marrow derived MSCs, gingiva derived MSCs, or combinations thereof. The composition thereby prepared may be used in a treatment of a mammal that has multiple myeloma, an inflammatory and/or autoimmune disease. Examples of the inflammatory and/or autoimmune diseases may be graft-versus-host disease (GvHD), diabetes, rheumatoid arthritis (RA), autoimmune encephalomyelitis, systemic lupus erythematosus (SLE), multiple sclerosis (MS), systemic sclerosis, osteoporosis, periodontitis, inflammatory bowel disease (IBD), alimentary tract mucositis induced by chemotherapy, alimentary tract mucositis induced by radiotherapy, or sepsis.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials which have been described and their equivalents. Similarly, the phrase "step for" when used in a claim is intended to and should be interpreted to embrace the corresponding acts which have been described and their equivalents. The absence of these phrases in a claim mean that the claim is not intended to and should not be interpreted to be limited to any of the corresponding structures, materials, or acts or to their equivalents.

Nothing which has been stated or illustrated is intended or should be interpreted to cause a dedication of any component, step, feature, object, benefit, advantage, or equivalent to the public, regardless of whether it is recited in the claims.

The scope of protection is limited solely by the claims which now follow. That scope is intended and should be interpreted to be as broad as is consistent with the ordinary meaning of the language which is used in the claims when interpreted in light of this specification and the prosecution history which follows and to encompass all structural and functional equivalents.

We claim:

1. A method of treating a mammal that has multiple myeloma (MM), comprising:
   a. obtaining a tissue comprising mesenchymal stem cells (MSCs);
   b. treating the tissue to activate or increase level of Fas-L expression, and thereby obtaining treated MSCs having highly expressed Fas-L;
   c. preparing a composition comprising the treated MSCs having highly expressed Fas-L; and
   d. administering a therapeutically effective amount of the composition to the mammal to treat the MM;
   wherein the treating the tissue comprises separating the tissue into cells, sorting the MSCs, and treating the MSCs with a solution comprising an effective amount of aspirin.

2. The treatment method of claim 1, wherein the MSCs comprise bone marrow derived MSCs.

3. The treatment method of claim 1, wherein the MSCs comprise gingiva derived MSCs.

4. The treatment method of claim 1, wherein the treatment inhibits at least MM cell growth.

5. The treatment method of claim 1, wherein the treatment inhibits at least tumor growth.

6. The treatment method of claim 1, wherein the treatment increases survival rate of the mammal that has MM.

7. The treatment method of claim 1, wherein concentration of aspirin in the solution is in the range of 1 µg/ml to 1,000 µg/ml.

8. The treatment method of claim 1, wherein concentration of aspirin in the solution is in the range of 5 µg/ml to 200 µg/ml.

9. The treatment method of claim 1, wherein concentration of aspirin in the solution is in the range of 25 µg/ml to 100 µg/ml.

10. The treatment method of claim 1, wherein the MSCs are treated for a duration in the range of 1 hour to 100 days.

11. The treatment method of claim 1, wherein the MSCs are treated for a duration in the range of 1 day to 20 days.

12. The treatment method of claim 1, wherein the MSCs are treated for a duration in the range of 3 days to 10 days.

13. The method of claim 1, wherein the MSCs are not bone marrow-derived mesenchymal stem cells.

* * * * *